United States Patent [19]

Soll et al.

[11] Patent Number: 5,677,800
[45] Date of Patent: Oct. 14, 1997

[54] VIEWING ASSEMBLY FOR PRODUCING AN OPTICALLY CORRECTED REFLECTED IMAGE

[75] Inventors: David B. Soll, Rydal, Pa.; Richard Evans Feinbloom, New York, N.Y.

[73] Assignee: Image Optical Corporation, Wilmington, Del.

[21] Appl. No.: 482,679

[22] Filed: Jun. 7, 1995

Related U.S. Application Data

[63] Continuation-in-part of Ser. No. 116,169, Sep. 2, 1993, Pat. No. 5,497,274.

[51] Int. Cl.[6] ............................................. G02B 5/08
[52] U.S. Cl. ........................ 359/846; 359/847; 359/849; 359/868
[58] Field of Search ............................. 359/838, 846, 359/847, 848, 849, 862, 863, 868, 869, 224

[56] References Cited

U.S. PATENT DOCUMENTS

| | | | |
|---|---|---|---|
| 1,685,032 | 9/1928 | Parsons | 359/849 |
| 2,579,225 | 12/1951 | Borst et al. | 359/849 |
| 2,733,637 | 2/1956 | Joseph | 88/96 |
| 3,004,472 | 10/1961 | Buxton | 359/846 |
| 3,374,047 | 3/1968 | Gatchell | 359/727 |
| 3,539,247 | 11/1970 | Broussard | 359/847 |
| 3,552,835 | 1/1971 | Benzies | 359/847 |
| 3,610,738 | 10/1971 | Bochmann | 359/847 |
| 3,623,793 | 11/1971 | Merten et al. | 359/847 |
| 3,623,796 | 11/1971 | Schweiger | 359/847 |
| 3,628,852 | 12/1971 | Snaper et al. | 359/849 |
| 3,677,620 | 7/1972 | Bettencourt | 359/817 |
| 3,733,116 | 5/1973 | Hutchinson | 359/847 |
| 3,776,637 | 12/1973 | Hecht | 359/868 |
| 3,781,095 | 12/1973 | Rushing et al. | 359/847 |
| 3,827,782 | 8/1974 | Boudouris et al. | 359/846 |
| 3,832,039 | 8/1974 | Doolittle | 359/846 |
| 3,893,755 | 7/1975 | Cobarg et al. | 359/847 |
| 3,970,369 | 7/1976 | Wachsman | 359/732 |
| 3,972,600 | 8/1976 | Cobarg | 359/847 |
| 3,996,947 | 12/1976 | Szpur et al. | 132/316 |
| 4,056,309 | 11/1977 | Harbison et al. | 359/847 |
| 4,119,366 | 10/1978 | Lemaitre | 359/847 |
| 4,128,310 | 12/1978 | Miller | 359/847 |
| 4,226,507 | 10/1980 | Fuschetto | 359/849 |
| 4,243,301 | 1/1981 | Powell | 359/847 |
| 4,261,655 | 4/1981 | Honigsbaum | 351/41 |
| 4,266,857 | 5/1981 | Svenson | 359/845 |
| 4,418,990 | 12/1983 | Gerber | 351/41 |
| 4,734,557 | 3/1988 | Alfille et al. | 359/847 |
| 4,913,536 | 4/1990 | Barnea | 359/666 |

FOREIGN PATENT DOCUMENTS

| | | | |
|---|---|---|---|
| 1475736 | 2/1967 | France | 359/849 |
| 2379078 | 8/1978 | France | 359/846 |
| 2255789 | 5/1974 | Germany | 132/316 |
| 2261679 | 6/1974 | Germany | 132/316 |
| 283136 | 11/1934 | Italy | 359/846 |
| 52-76046 | 6/1977 | Japan | 359/849 |
| 68-198207 | 9/1986 | Japan | 359/846 |
| 1418636 | 8/1988 | U.S.S.R. | 359/846 |
| 2 152 701 | 8/1985 | United Kingdom | G02B 7/18 |

OTHER PUBLICATIONS

Drawings (Figs. 1–24) for DE 2255789, published May 1974.

Hardy, J.W., "Active Optics: A New Technology for the Control of Light", Proceedings of the IEEE, vol. 66, No. 6, Jun. 1978, 651–697.

*Primary Examiner*—Paul M. Dzierzynski
*Assistant Examiner*—John Juba, Jr.
*Attorney, Agent, or Firm*—Panitch Schwarze Jacobs & Nadel, P.C.

[57] ABSTRACT

The present invention is a viewing assembly that can selectively create optical compound corrections in the images reflected from the viewing assembly. The viewing assembly includes a reflective surface coupled to a supporting body in such a manner that the reflective surface conforms to the contour of the supporting body. The contour of the supporting body is selectively altered by the viewer of the viewing assembly, thereby changing the shape of the reflective surface and creating desired optical corrections in the viewed reflected images.

6 Claims, 14 Drawing Sheets

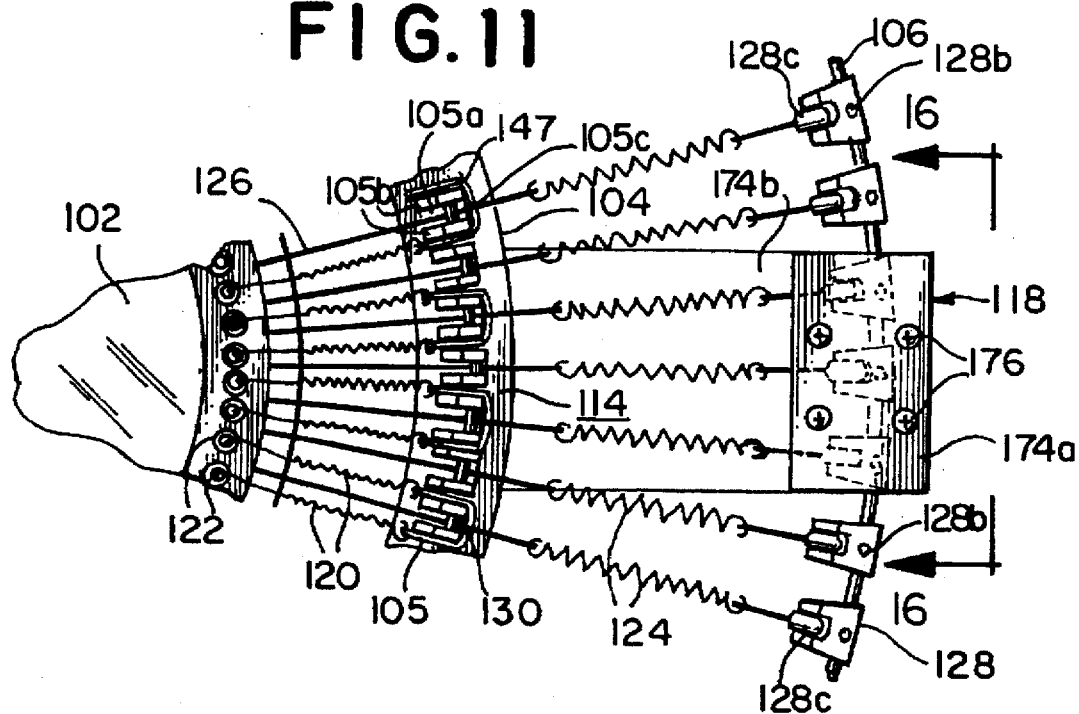
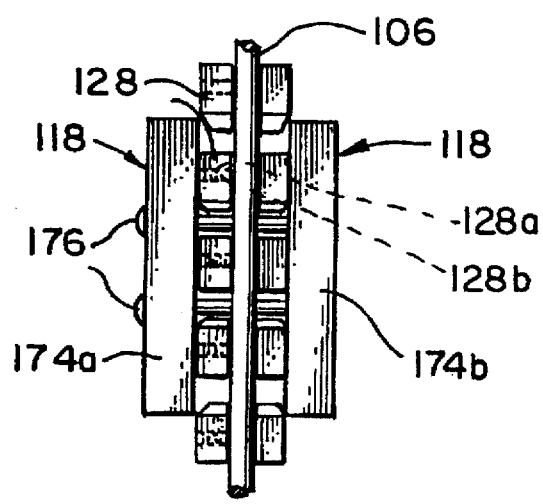

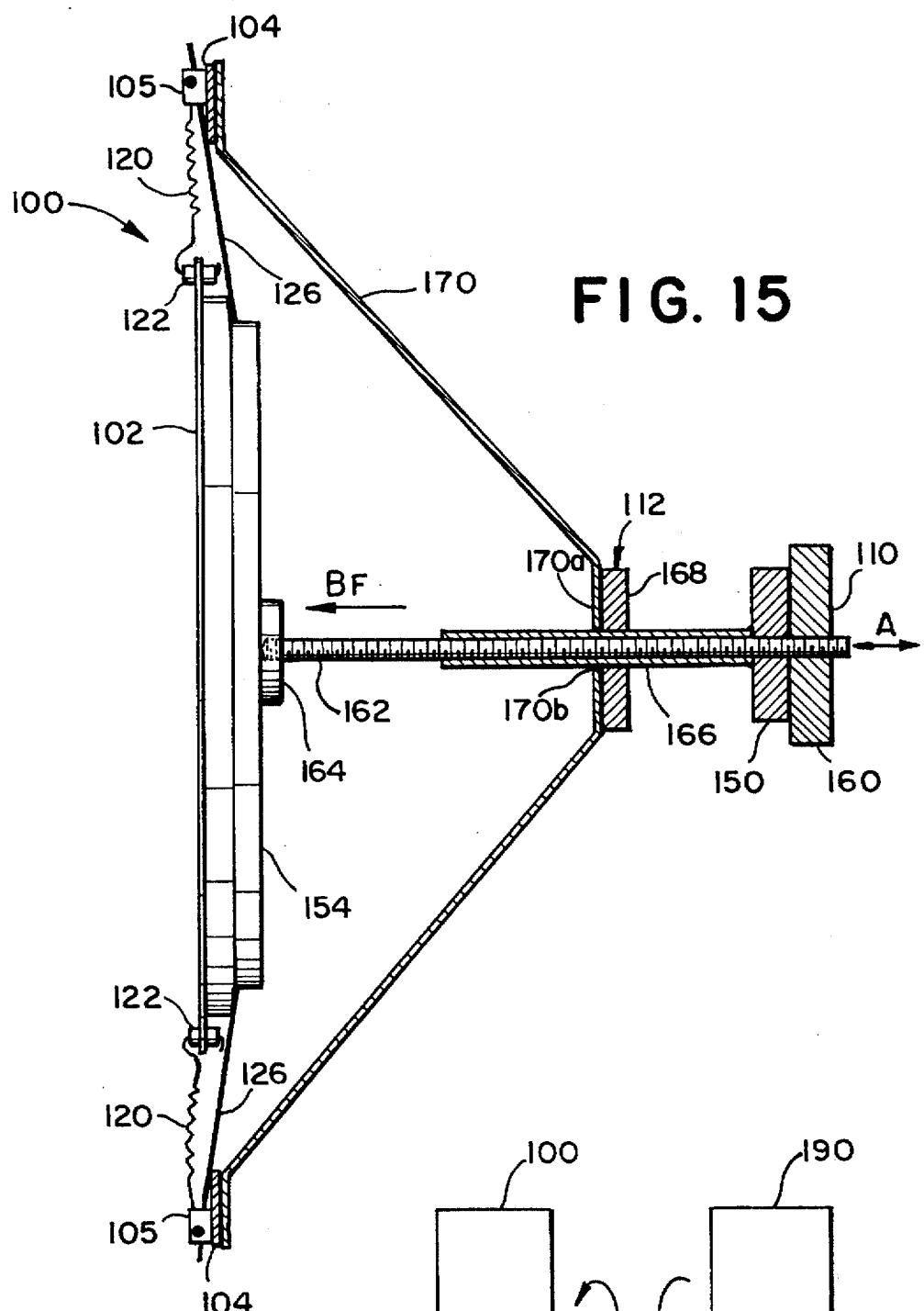

VIEWING ASSEMBLY FOR PRODUCING AN OPTICALLY CORRECTED REFLECTED IMAGE

CROSS-REFERENCE TO RELATED APPLICATION

This application is a continuation-in-part of application Ser. No. 08/116,169 filed Sep. 2, 1993, also entitled "VIEWING ASSEMBLY FOR PRODUCING AN OPTICALLY CORRECTED REFLECTED IMAGE," now U.S. Pat. No. 5,497,274.

FIELD OF THE INVENTION

The present invention relates to a viewing assembly that corrects a reflected image in such a manner so as to compensate for an imperfection in the viewer's eyesight and, more particularly, to such viewing assemblies that can selectively provide optical corrections to a reflected image corresponding to the needs of the viewer.

BACKGROUND OF THE INVENTION

Many people have imperfect vision that requires correction through the use of prescriptive lenses. However, it is not always desirable or practical to use prescriptive lenses when performing certain tasks that require accurate vision. For example, when a person views himself or herself in a mirror for the purpose of shaving, applying cosmetics, or the like, clear vision is obviously desired. However, the use of eyeglasses in such situations is impractical because conventional eyeglasses obstruct the person's face. Another situation where wearing prescriptive lenses is impractical, is when a person is selecting spectacle frames to support their prescriptive lenses. In such a situation, the person selecting the spectacle frames cannot clearly view his or her image in a plano or flat mirror unless the needed prescriptive lenses are held in front of the frames being sampled. This, however, obstructs part of the reflective image the person is trying to view.

Mirrors are optical devices that reflect light, in accordance with the contours of their reflective surfaces. As such, mirrors can be formed with varied focal points so as to compensate for any one person's visual imperfections. However, most every person's visual impairments differ from those of other persons. Therefore, it is impossible to form a single fixed mirror surface that can compensate for the visual imperfections of all, or even most, people. As such, mirrors have been invented that have variable focal lengths in an attempt to allow each person to adjust the mirror to best correct his or her own vision.

Some of the simplest ways to produce a variable mirror focal point is to place a corrective lens in front of a fixed flat mirror. The corrective lens may include custom formed lenses or the corrective lens may be adjustably positioned relative to the flat mirror, thereby allowing the focal length of the mirror to be altered. The prior art of such corrective lens mirrors is exemplified in U.S. Pat. No. 3,374,047 to Gatchell; U.S. Pat. No. 3,677,620 to Bettencourt and U.S. Pat. No. 3,970,369 to Wachsman. As can be recognized by a person skilled in the art, the variability of such corrective lens mirrors is limited by the optical characteristics of the corrective lens being used. Therefore, one mirror cannot be created for use by all people regardless of their visual impairment.

A second prior art method of varying the focal length of a mirror is accomplished by selectively varying the contour of the mirror surface. In such systems, the mirror surface is formed on a flexible backing, thereby allowing the mirror surface to be flexed into a convex or concave orientation. In some systems, such as U.S. Pat. No. 2,733,637 to Joseph, the mirror surface is flexed by compressing the frame of the mirror. Another common means of deforming the mirror is through the use of pneumatics or hydraulics, creating a fluid pressure on one side of the mirror that causes it to deform. Such pneumatic or hydraulic mirror systems are exemplified in U.S. Pat. No. 3,623,793 to Mertem; U.S. Pat. No. 3,632,796 to Schweiger; U.S. Pat. No. 3,972,600 to Cobary; U.S. Pat. No. 4,119,366 to LeMaitre; U.S. Pat. No. 4,128,310 to Miller and U.S. Pat. No. 4,913,536 to Barnea. Additionally, the deformation of optical elements using a pneumatic means have also been used in applications other than that of corrective mirrors. For example, in U.S. Pat. No. 4,261,655 to Honigsbaum, there is shown a pneumatic method used to shape prescriptive lenses within a pair of eyeglasses.

The problem inherent in the pneumatically or hydraulically deformed mirrors of the prior art is that the pressure used to deform the mirror surface, produces only a spherical concave or convex correction to the reflected image. However, many people who wear glasses have corrective lenses that create cylindrical or torical corrections in a viewed image. The conventional prior art systems are incapable of producing cylindrical or torical corrections in the reflected image, therefore limiting the ability of prior art mirror systems to accurately compensate for prescriptive lenses.

It is therefore a primary objective of the present invention to provide a viewing assembly that reflects an image that can be adjustably corrected spherically, cylindrically and/or torically, thereby allowing the present invention viewing assembly to correct a reflected image in a more accurate manner.

SUMMARY OF THE INVENTION

The present invention comprises a viewing apparatus including a flexible body having a reflective front surface for reflecting an image. A first adjustment mechanism is operatively engaged with the flexible body. The first adjustment mechanism varies the radius of curvature of the front surface of the flexible body such that the front surface is in the form of a partial sphere, thereby providing a spherical correction in the image. A second adjustment mechanism, different from the first adjustment mechanism, is operatively engaged with said flexible body. The second adjustment mechanism varies the cylindrical curvature of the front surface of the flexible body such that the front surface is in the form of a partial cylinder, thereby providing a cylindrical correction in the image whereby selective adjustments of the first and second adjustment mechanisms provide one of either a spherical, cylindrical or toric correction in the image.

BRIEF DESCRIPTION OF THE DRAWINGS

For a better understanding of the present invention, reference is made to the following descriptions of exemplary embodiments thereof, considered in conjunction with the accompanying drawings, in which:

FIG. 11 is an enlarged fragmentary front elevation view of a portion of the viewing assembly in FIG. 10;

FIG. 15 is a cross-sectional side view of FIG. 10 of parts of an optical adjustment mechanism associated with the fifth embodiment of the present invention viewing assembly, taken along lines 15—15 of FIG. 10;

FIG. 16 is a sectional view of FIG. 11, taken along line 16—16 of FIG. 11; and

FIG. 17 is a diagrammatical view of an axis adjustment mechanism associated with the fifth embodiment of the present invention viewing assembly.

DETAILED DESCRIPTION OF THE PREFERRED EMBODIMENTS

Figure 1:
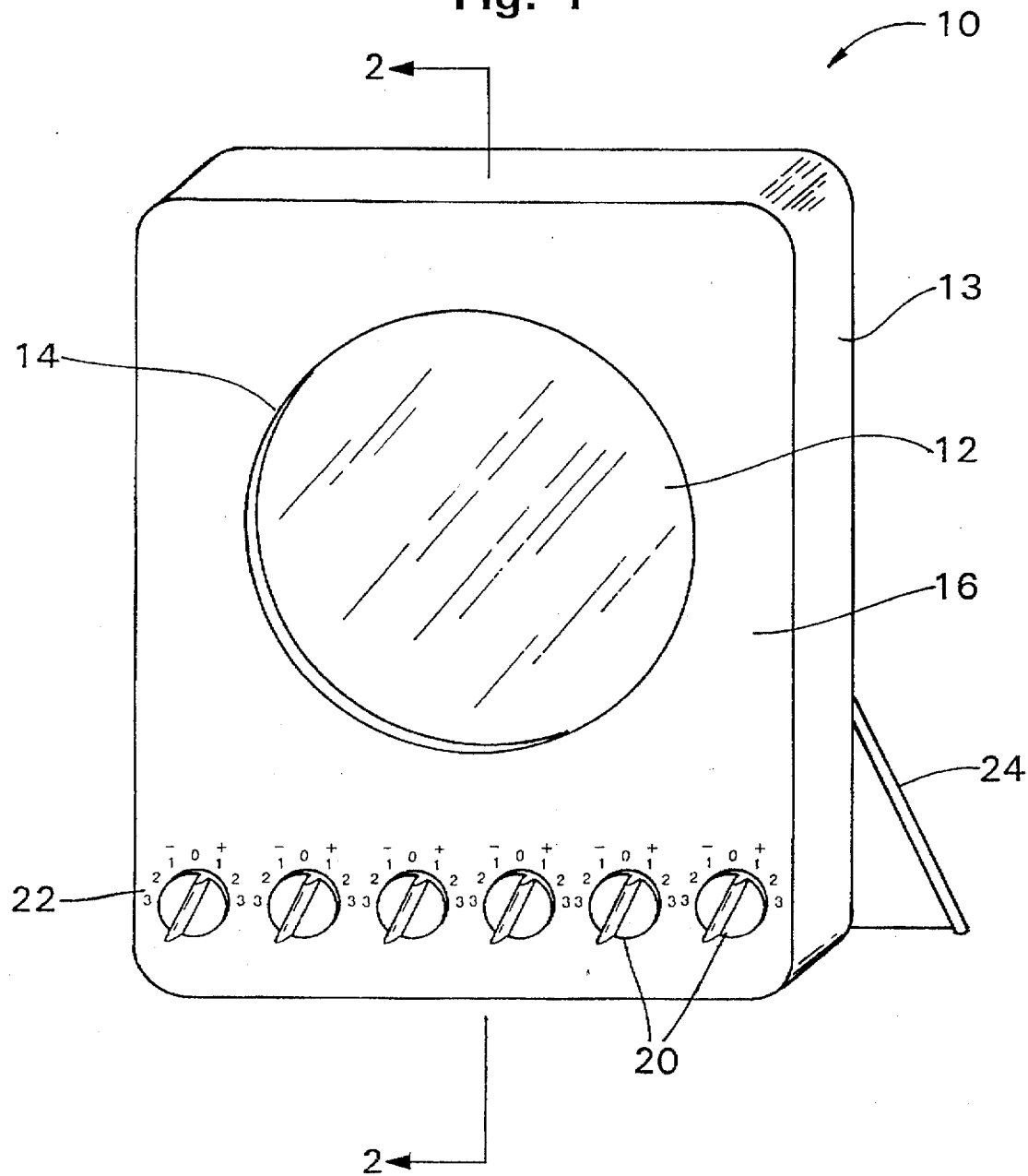
FIG. 1 is a perspective view of one preferred embodiment of the present invention viewing assembly.

Each person's eyesight is unique to that person, and for that reason eyeglasses are produced by prescription for the specific visual imperfections of an individual. The strength of individual lenses is dependent upon the index of refraction for the material of the lens, the thickness of the lens and the surface curvatures of the lens surfaces. The material, thickness and curvature characteristics of a set of lenses are then matched with the needs of an individual, to produce the needed visual corrections.

In producing corrective lenses for eyesight, there are three primary surface shapes into which the surface of a corrective lens is usually formed. The first surface is a spherical surface. A spherical surface is that found along the surface of a ball, wherein all points on the spherical surface share a common radius to a single common point. Therefore, the radius of curvature for a spherical surface is constant across the entire spherical surface.

In many applications, corrective lenses are needed with a surface curvature that is not spherical. Therefore, a lens surface can be formed into the shape of a cylindrical surface. A cylindrical curvature is that found on a surface of a cylinder. A cylindrical surface has a single radius of curvature as measured at a perpendicular from the longitudinal axis of the cylinder. However, the longitudinal axis of the cylinder is not curved. As such, a cylindrical surface has a meridian that has substantially no optical power. The meridian of no optical power is conventionally known as the axis of the cylindrical surface.

The third type of surface shape, into which a corrective lens can be formed, is a toric surface. A toric surface is a combination of a spherical surface with a cylindrical surface. As such, in a toric surface, the curvature of the surface along each meridian is different and no meridian lacks optical power. In modern corrective lenses, toric surfaces are used more commonly than are cylindrical surfaces or spherical surfaces alone.

As will be recognized by a person skilled in the art, the curvature of a lens surface is referred to as a diopter. A diopter is a measure of the power of a lens equal to the reciprocal of its focal length in meters. For instance, a one diopter lens has a focal length of one meter. The ordinary range of toric lens curvatures, including practically all commonly used lens surfaces, spans from plus or minus zero to twenty diopters of spherical power to four cylindrical diopters in one quarter diopter steps. Additionally, diopter values are usually denoted as being either negative (−) or positive (+), so as to denote the curvature of a concave surface or convex surface, respectively. However, it is understood by those of ordinary skill in the art from this disclosure that the present invention is not limited to any particular range of toric lens curvature, and is equally applicable to ranges outside of the ordinary range mentioned above.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the viewing assembly and designated parts thereof. The terminology includes the words above specifically mentioned, derivatives thereof and words of similar import.

Referring to FIG. 1, an embodiment of the present invention viewing assembly 10 is shown having a reflective surface 12 positioned within a housing 13. A view window 14 is formed through the face surface 16 of the housing 13 so that a person viewing the face surface 16 of the housing 13 can see the reflective surface 12. A plurality of adjustment knobs 20 are positioned below the view window 14 on the face surface 16 of the housing 13. As will be later explained, the adjustment knobs 20 control the curvature of the reflective surface 12, thereby enabling the curvature of the reflective surface 12 to be selectively adjusted as desired. Reference numerals 22 or other indicia are disposed around each of the adjustment knobs 20 to provide a reference as to the rotational position of each of the adjustment knobs 20. As will be later explained, the reference numerals 22 can be used to apply a desired curvature to the reflective surface 12 that corresponds to a specific eyeglass prescription. The viewing assembly 10 may include a support stand member 24 or similar device used to support the viewing assembly 10 upright at a desired angle of inclination. It is understood by those skilled in the art that the present invention is not limited to counter top or desk top use. That is, the viewing assembly 10 could be sized as a full length mirror to allow a person to view their entire body without the use of corrective lenses or could be sized as a compact hand-held mirror.

Figure 2:
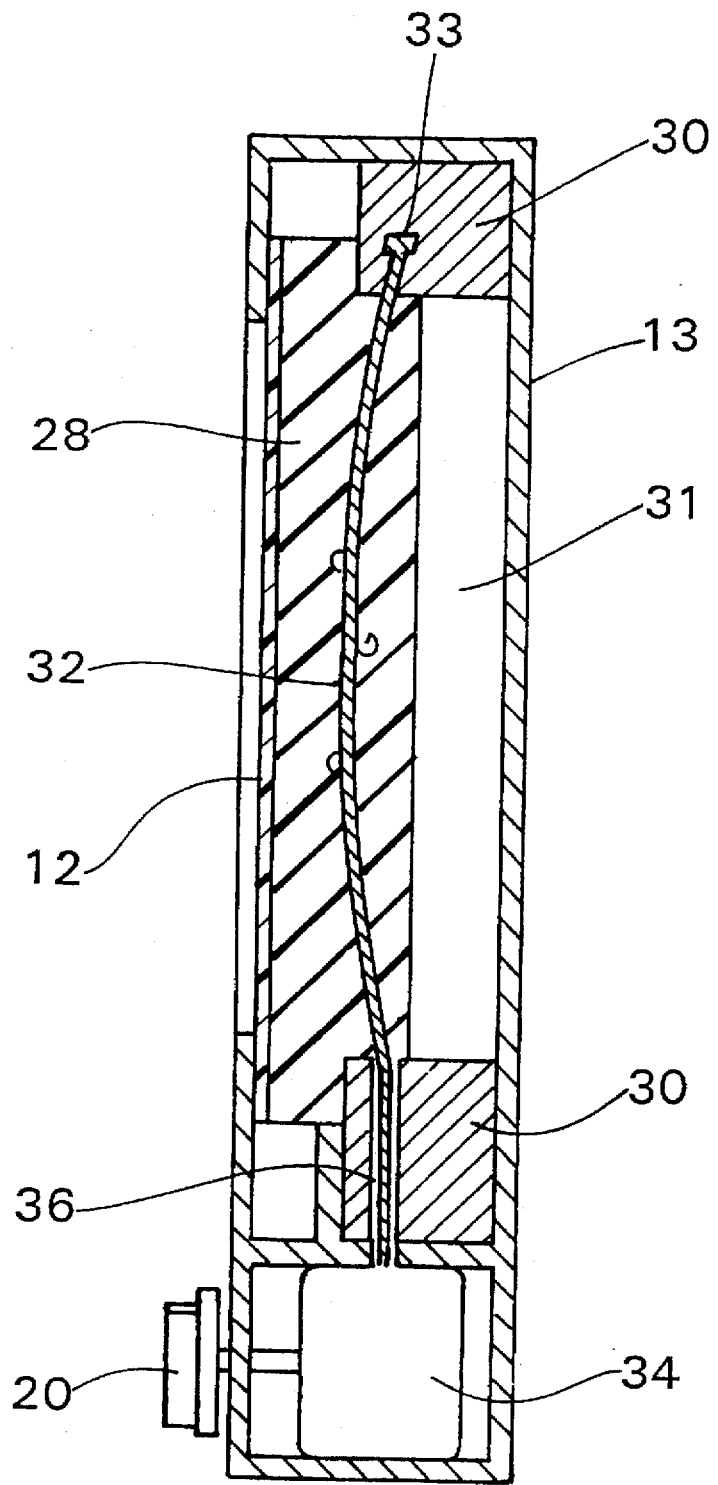
FIG. 2 is a cross-sectional view of the embodiment of the present invention shown in FIG. 1, viewed along section line 2—2.

Referring to FIG. 2, it can be seen that the reflective surface 12 is disposed upon a flexible or formable body 28 (hereinafter "flexible body 28"). In the present embodiment, it is preferred that the body 28 be formed of an elastomeric material, such as silicone or GERTV. However, it is understood by those skilled in the art that the body 28 could be constructed of other flexible or formable materials, such as isoprene rubbers, natural rubbers, CIS polyisoprene rubbers, neoprene rubbers, butyl rubbers, nitrile copolymers, silicone, hypalon, acrylic, thiokol or polyurethane. The flexible body 28 is seated within a rigid frame structure 30 inside the housing 13. The rigid frame structure 30 surrounds an open central region 31. The flexible body 28 is shaped to abut against one side of the rigid frame structure 30 and partially extend into the open central region 31. Although the rigid frame structure 30 is shown as a separate element, it should be understood that the rigid frame structure 30 can be unistructurally formed as part of the mirror housing 13.

In the present embodiment, it is preferred that the reflective surface 12 be constructed of a flexible mirror material, such as a thin metal coated polymer. Examples of the metal coated polymers include aluminized polyesters or MYLAR®. It is understood by those skilled in the art that other flexible reflective materials could be used without departing from the spirit and scope of the invention. The reflective surface 12 is preferably bonded to the flexible body 28 by a suitable bonding process within the knowledge of those skilled in the art.

The flexible body 28 is mechanically joined to the rigid frame structure 30 by a plurality of flexible generally elongate members 32. In the shown embodiment, each flexible member 32 has one end 33 that is anchored to the rigid frame structure 30. Each of the flexible members 32 extends through the flexible body 28, following a predetermined curvature. Each flexible member 32 exits the flexible body 28 and enters a conduit 36 in the rigid frame structure 30 at a point opposite its anchored end 33. The flexible members 32 pass through the conduits 36 and are each coupled to a tensioning mechanism 34 below the rigid frame structure 30. The tensioning mechanisms 34 are controlled by the adjustment knobs 20 that extend through the housing 13. The tensioning mechanisms 34 can be any known assembly capable of advancing the flexible members 32 into, and retracting the flexible members 32 from, the conduits 36 in the rigid frame structure 30, such as a spool (not shown) secured to an adjustment knob. The passage of the flexible members 32 within various conduits 36, prevents the bending or buckling of the flexible members 32 within the rigid frame structure 30, as the flexible members 32 are selectively advanced by the tensioning mechanisms 34. As will be later explained, by selectively adjusting the tensioning mechanisms 34, the curvature of the flexible member 32 within the flexible body 28 can be changed, resulting in a change in the shape of a flexible body 28 and a corresponding change in the curvature of the reflective surface 12.

Figure 3:
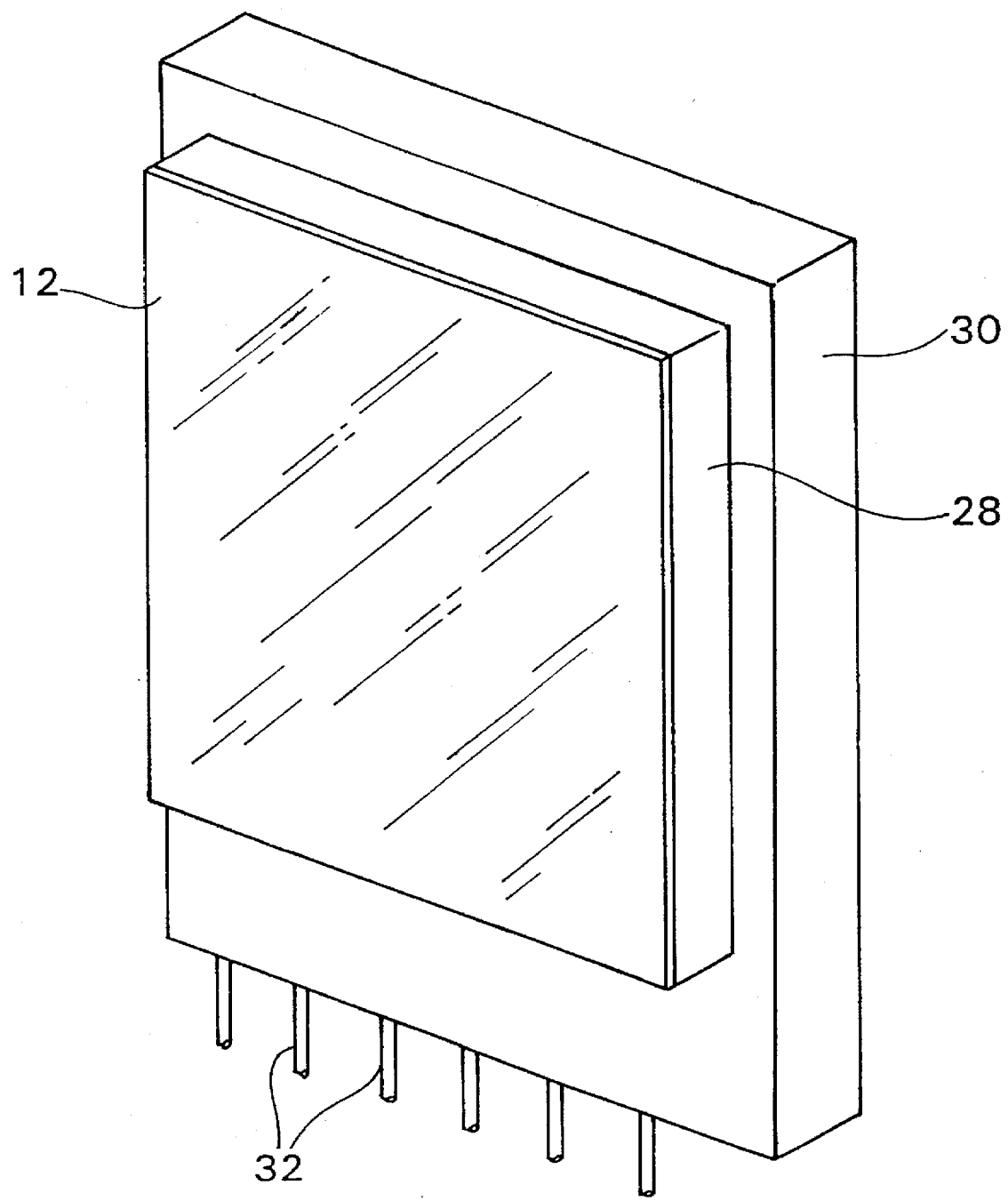
FIG. 3 is an isolated perspective view of the reflective surface, of the present invention viewing assembly, disposed upon an elastomeric body and held within a rigid frame structure in accordance with a preferred construction of the present invention.

In FIG. 3, there is shown an isolated view of the flexible body 28 and reflective surface 12, seated within the rigid frame structure 30. As can be seen, the flexible body 28 abuts one side of the rigid frame structure 30 and covers the area of the open center region 31 (shown in FIG. 2). The flexible body 28 fills at least part of the open center region 31 such that the flexible members 32 extend through the flexible body 28 as the flexible members 32 pass across the open center region 31 within the rigid frame structure 30.

Figure 4:
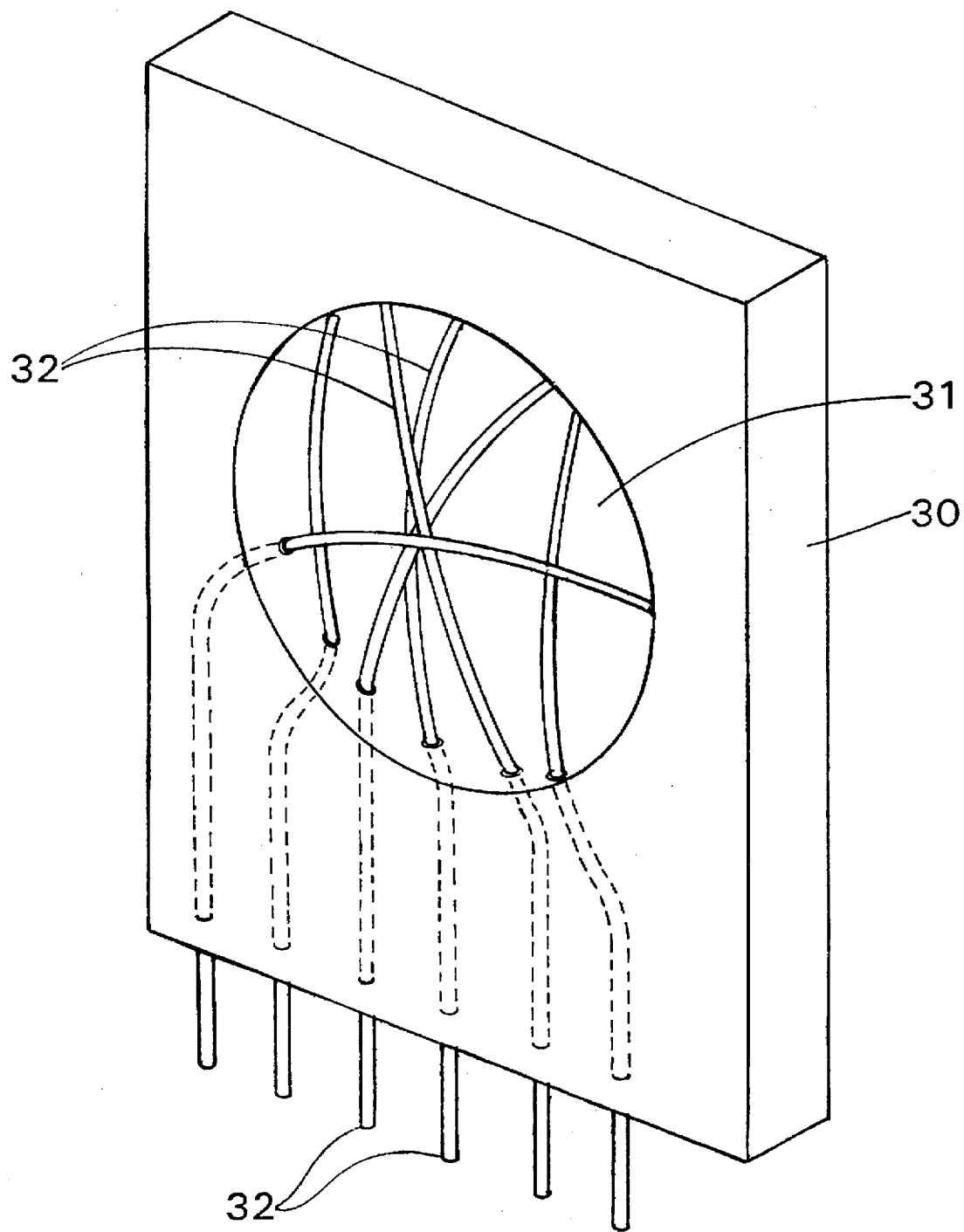
FIG. 4 is an isolated perspective view of the rigid frame structure of the present invention viewing assembly, shown without the presence of the elastomeric body to facilitate discussion and consideration.

Referring to FIG. 4, the rigid frame structure 30 and flexible members 32 are shown without the reflective surface 12 or the material of the flexible body 28, as was previously shown in FIG. 3. As can now be seen, the flexible members 32 traverse the open center region 31 of the rigid frame structure 30 at a plurality of orientations. In the shown embodiment, there are six flexible members 32, however, it should be understood that any plurality can be used. The flexible members 32 can be made of any strong flexible material, such as wire or flat strapping, so long as the flexible members 32 bend when compressed and become linear when made taut. In the present embodiment, the wires are preferably constructed of music wire and have a diameter equal to approximately 0.035 inches. The various flexible members 32 can be arranged in any orientation, wherein the flexible members 32 may lay in parallel rows so as to create an overall cylindrical shape, or may crisscross cross each other's path, to create an overall spherical shape. Regardless of the selected orientations of the flexible members 32, each of the flexible members 32 is initially compressed to bow outwardly along a predetermined curved path as the flexible members 32 cross the open center region 31. However, the curved path followed by each of the flexible members 32 need not be the same. Each of the flexible members 32 is initially oriented to follow a desired spherical cylindrical curvature which produces a toric curve that spans the open center region 31. Although the curvature of each of the flexible members 32 can be the same, in a preferred embodiment, one, or any plurality of flexible members 32, may follow a spherical curvature while the other flexible members 32 follow a cylindrical curvature. If some of the flexible members 32 follow spherical curves and others follow cylindrical curves, the combination of the flexible members 32 creates an overall toric surface across the open center region 31. The initial curvatures of each of the flexible members 32 are preserved in a first position as the material of the flexible body 28 (shown in FIG. 3) is molded around the flexible members 32 within the open center region 31. Consequently, each of the flexible members 32 is enveloped by the flexible body 28 and each of the flexible members 32 retains its initial curvature by the presence of the material of the flexible body 28 surrounding each flexible member 32.

Figure 5A:
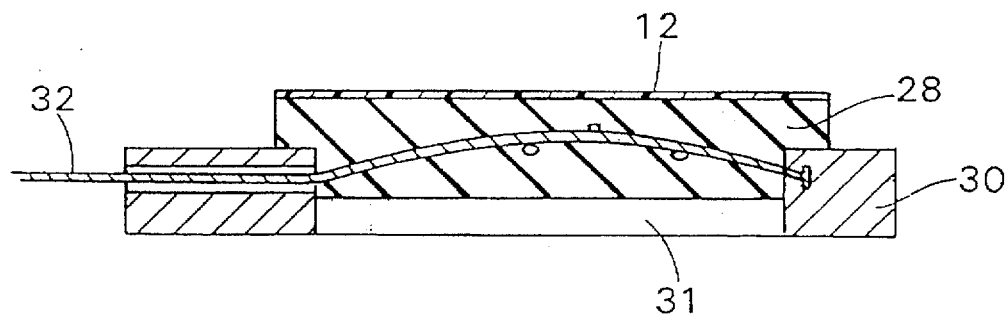
FIGS. 5a, 5b and 5c are isolated cross-sectional views of the reflective surface and supporting elastomeric body, of the present invention viewing assembly, selectively formed into three separate curvatures so as to facilitate consideration and discussion of the operation of the present invention.

Referring to FIG. 5a, a cross section of the flexible body 28 seated within the rigid frame structure 30 is shown. When the flexible members 32 are in the first position each flexible member 32 follows its initial spherical or cylindrical curvature within the material of the flexible body 28. The flexible body 28 is shaped so that the reflective surface 12 lays in a flat plane when the flexible members 32 are in the first position. However, when the tensioning mechanisms (shown in FIG. 2) are manipulated to advance one or more flexible members 32 toward the flexible body 28, the effected flexible members 32 bend outwardly, and change from the initial curvature of the first position to a more curved orientation.

Figure 5B:
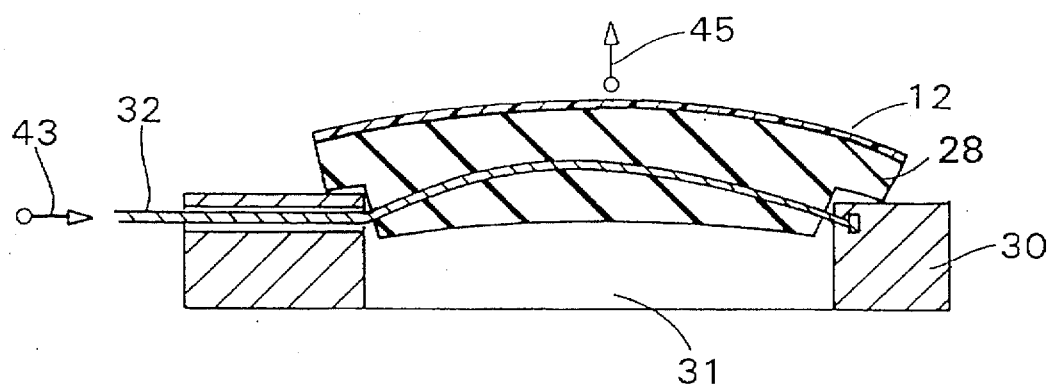

Referring to FIG. 5b, it can be seen that as a flexible member 32 is increasingly advanced in the direction of arrow 43, the curvature of the flexible member 32 changes. Each flexible member 32 bows in an even manner, creating a semicircular path from one end of the open center region 31, to the other. The more a flexible member 32 is advanced, the smaller the radius of curvature for a semicircular path becomes. Since each flexible member 32 is enveloped by the material of the flexible body 28, the bending of the flexible members 32 causes the flexible body 28 to deform outwardly in the direction of arrow 45. The resulting deformation of the flexible body 28 causes the reflective surface 12 to deform, thereby altering the reflective characteristics of the reflective surface 12. Each of the flexible members 32 extends across the open center region 31 and passes through the flexible body 28 along a different line. Some of the flexible members 32 cross over the middle of the open center region 31 while other flexible members 32 only extend across a small segment of the open center region 31. Consequently, as each of the flexible members 32 is advanced by the tensioning mechanism, the change in curvature in each of the flexible members 32 creates a distinct change in curvature to the portion of the flexible body 28 near which that particular flexible member 32 passes. In the shown embodiment, there are six flexible members 32, as such the deformation of the flexible body 28 can be controlled by applying a tension or compression force, in any possible combination, to the six flexible members 32. As a result, the flexible body 28 can be adjusted along six different meridians, thereby allowing the reflective surface to be selectively adjustable along six separate meridians. Consequently, most any spherical or cylindrical curvatures can be created to produce a desired toric curve in the flexible body 28, wherein the toric curve is transferred to the reflective surface 12.

Figure 5C:
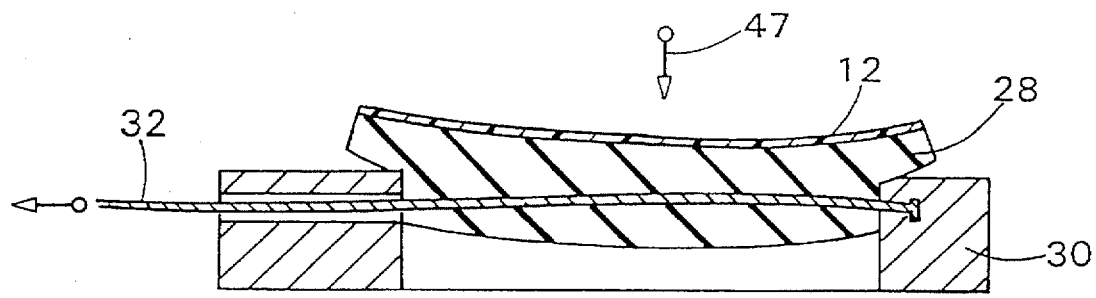

Furthermore, if the tensioning mechanisms or force adjustment devices (shown in FIG. 2) are manipulated to apply tension to one or more of the flexible members 32, the effected flexible members 32 change to a less curved orientation. Referring to FIG. 5c, it can be seen that as a flexible member 32 is increasingly made taut, the curvature of the flexible member 32 becomes less pronounced. The straightening of the flexible members 32 also causes the flexible body 28 to deform inwardly in the direction of arrow 47. The resulting deformation of the flexible body 28 is transferred to the reflective surface 12. Consequently, by adding the ability of making the flexible members 32 taut, the range of adjustments for the reflective surface is increased and the reflective surface 12 can be selectively adjusted to optically correct a larger range of eyesight imperfections.

While in the present embodiment it is preferred that the flexible members 32 have an initial curvature when the reflective surface 12 lies generally in a flat plane (as shown in FIG. 5a), it is understood by those skilled in the art that the particular initial orientation of the flexible members 32 with respect to the shape of the reflective surface 12 could be different. For instance, the flexible members 32 could lie in a generally flat plane when the reflective surface 12 is positioned in a generally flat plane such that the flexible members 32 and reflective surface 12 extend generally parallel with respect to each other, initially. The flexible members 32 could then be deformed upwardly to cause the reflective surface 12 to deform as shown in FIG. 5b. Similarly, the flexible members 32 could be flexed downwardly to cause the reflective surface 12 to deform to the shape shown in FIG. 5c. The particular manner in which the flexible members 32 are caused to flex upwardly or downwardly could be accomplished by allowing the conduits 36 to be angularly adjustable. That is, the conduits 36 could be angled upwardly to cause the flexible members 32 to flex upwardly or the user could select to angle the conduits 36 downwardly to cause the flexible members 32 to flex downwardly.

As is shown in FIG. 1, reference numerals 22 or other indicia are printed around each adjustment knob 20. Since the present invention viewing assembly 10 can be selectively adjusted across a wide range of configurations, a chart or similar structural device may be provided that indicates to a person where to set the various adjustment knobs 20 in order to obtain a desired correction in the reflected surface 12. As such, a person need only turn the adjustment knobs 20 to a position that corresponds to their eyeglass lens prescription in order to optically correct the reflective surface 12 to their individual needs.

In the shown embodiment of FIGS. 2–5c, the flexible members 32 were preset at a generally convex curvature making it easy to create convex deformations in the flexible body 28 and the reflective surface 12. However, it will be understood that flexible members 32 that initially follow a concave curvature can also be disposed within the flexible body 28, thereby increasing the range of concave deformations that can be selectively created in the flexible body 28 and reflector surface 12.

While in the present embodiment, it is preferred that the shape of the flexible body 28 be controlled by the flexible members 32 and adjustment knobs 20, it is understood by those skilled in the art that other methods could be used to control the shape of the flexible body 28. For instance, the flexible body 28 could be surrounded by a contractible ring (not shown) or retractable fingers (not shown) could extend inwardly from the frame 30 for supplying pressure to the circumference of the flexible body 28. Similarly, the present invention is not limited to the use of manually adjustable knobs 20. The position of the flexible members 32 can be automatically controlled. For instance, the tensioning mechanisms 34 could be coupled to stepper motors (not shown) which are controlled by a microprocessor (not shown) which can actuate the stepper motors and tensioning mechanisms 34 to a position which corresponds to a particular prescription input into a key pad or other input mechanism (not shown). Further, an infrared or other autofocusing system (not shown), once the particular prescription was input into the microprocessor, could automatically adjust the focal length of the reflective surface 12.

Figure 6:
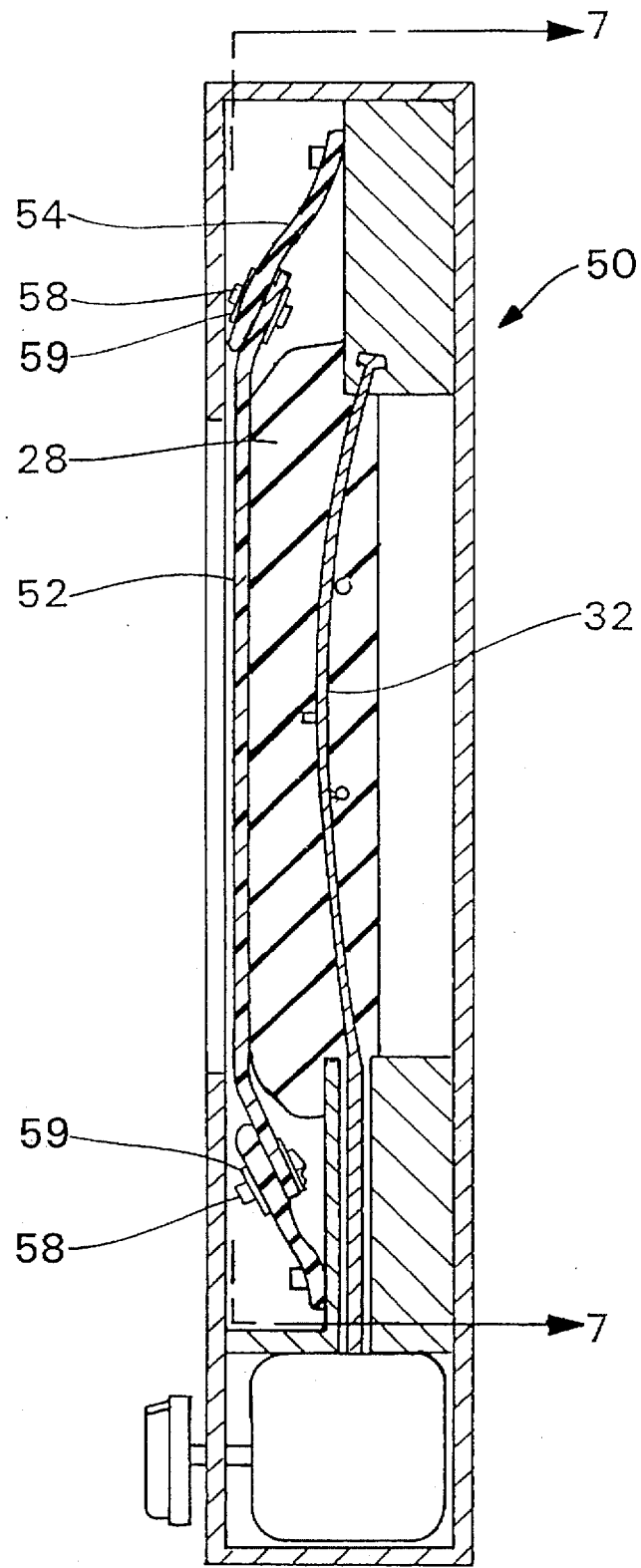
FIG. 6 is a cross-sectional view of an alternate embodiment of the present invention viewing assembly.
Figure 7:
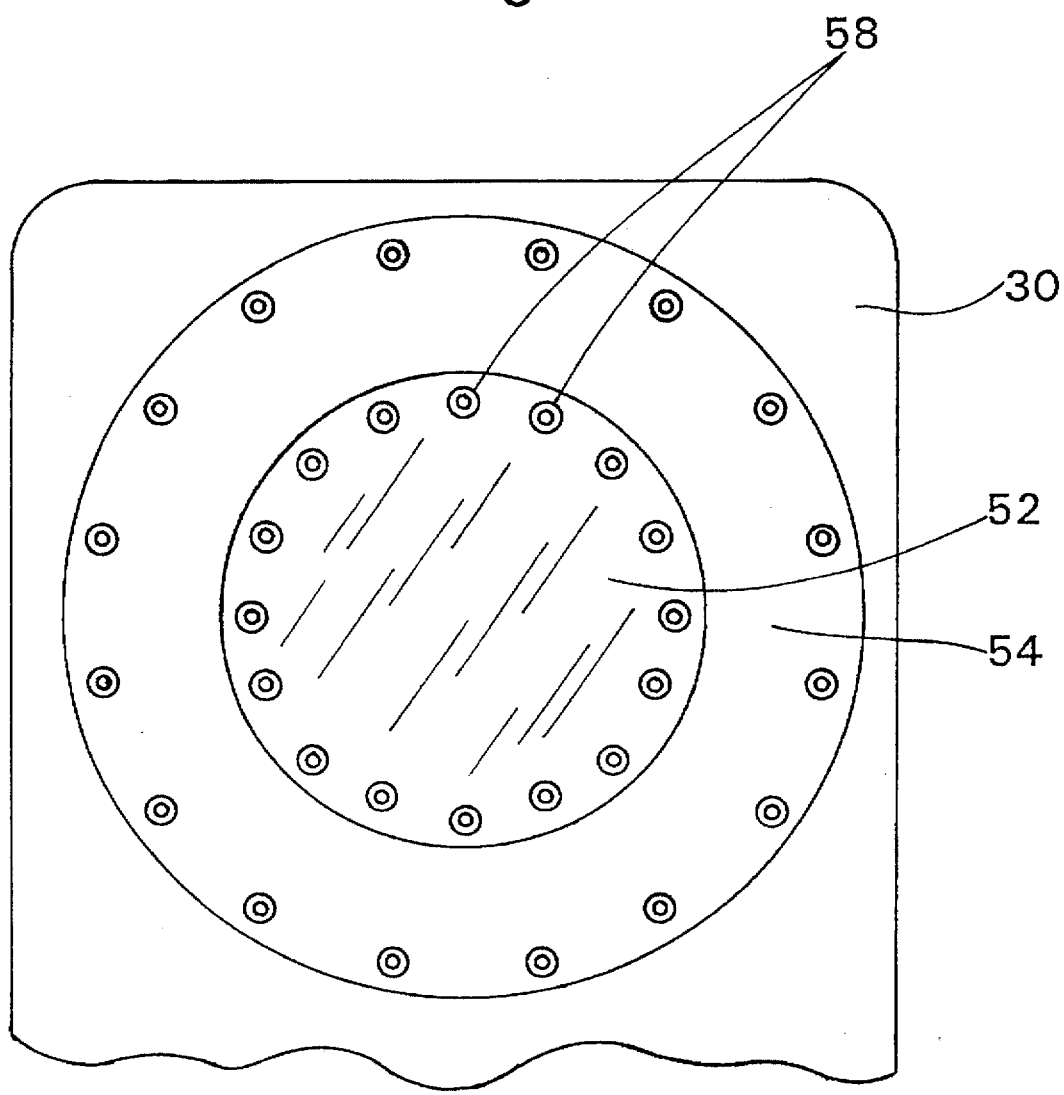
FIG. 7 is a forward view of the alternate embodiment of FIG. 6, viewed along section line 7—7.

Referring to FIG. 6, an alternative embodiment of the present invention viewing assembly 50 is shown. In this embodiment, the reflective surface 52 is not formed upon the flexible body 28, as has been previously described, but is biased against the flexible body 28. The flexible body 28 is deformed by the manipulation of the flexible members 32 that travel through the flexible body 28, as has been previously described. Referring to FIG. 7 in conjunction with FIG. 6, it can be seen that the reflective surface 52 is a sheet of reflective material, such as MYLAR®, pulled taut around its periphery by an elastic ring 54. The elastic ring 54, in turn, is attached to the rigid frame structure 30 that surrounds the flexible body 28. The reflective surface 52 is attached to the elastic ring 54 with a plurality of mechanical fasteners 58 that are symmetrically disposed around the periphery of the reflective surface 52. Each mechanical fastener 58 may include plastic washers 59 to help interconnect the reflective surface 52 to the elastic ring 54 by expanding the area of contact between each component. However, it will be understood that the reflective surface 52 can be attached to the elastic ring 54 in any manner, such as through the use of adhesives or by sewing the two components together along a seam. The elastic ring 54 is preferably constructed of latex sheet rubber or gum sheet rubber with a thickness in the range of $1/32$ to $1/16$ inches. The elastic ring 54 can be attached to the rigid frame structure 30 utilizing any known means of attachment. The elastic ring 54 is stretched between the reflective surface 52 and the rigid frame support 30. Consequently, the elastic ring 54 biases the reflective surface 52 against the flexible body 28 and the reflective surface 52 is held taut against the flexible body 28 without wrinkles or creases.

Since the reflective surface 52 is held taut against the flexible body 28, the reflective surface 52 conforms to the flexible body 28 such that any deformations in the flexible body 28 are transferred to the reflective surface 52. As such, by selectively creating spherical and/or cylindrical shape adjustments in the flexible body 28, the reflective surface 52 can be shaped along any desired toric curvature, thereby creating an optical correction as desired. Spherical and/or cylindrical changes in the shape of the flexible body 28 are created by selectively applying tension and compression forces to the flexible body 28, as has been previously described.

Figure 8:
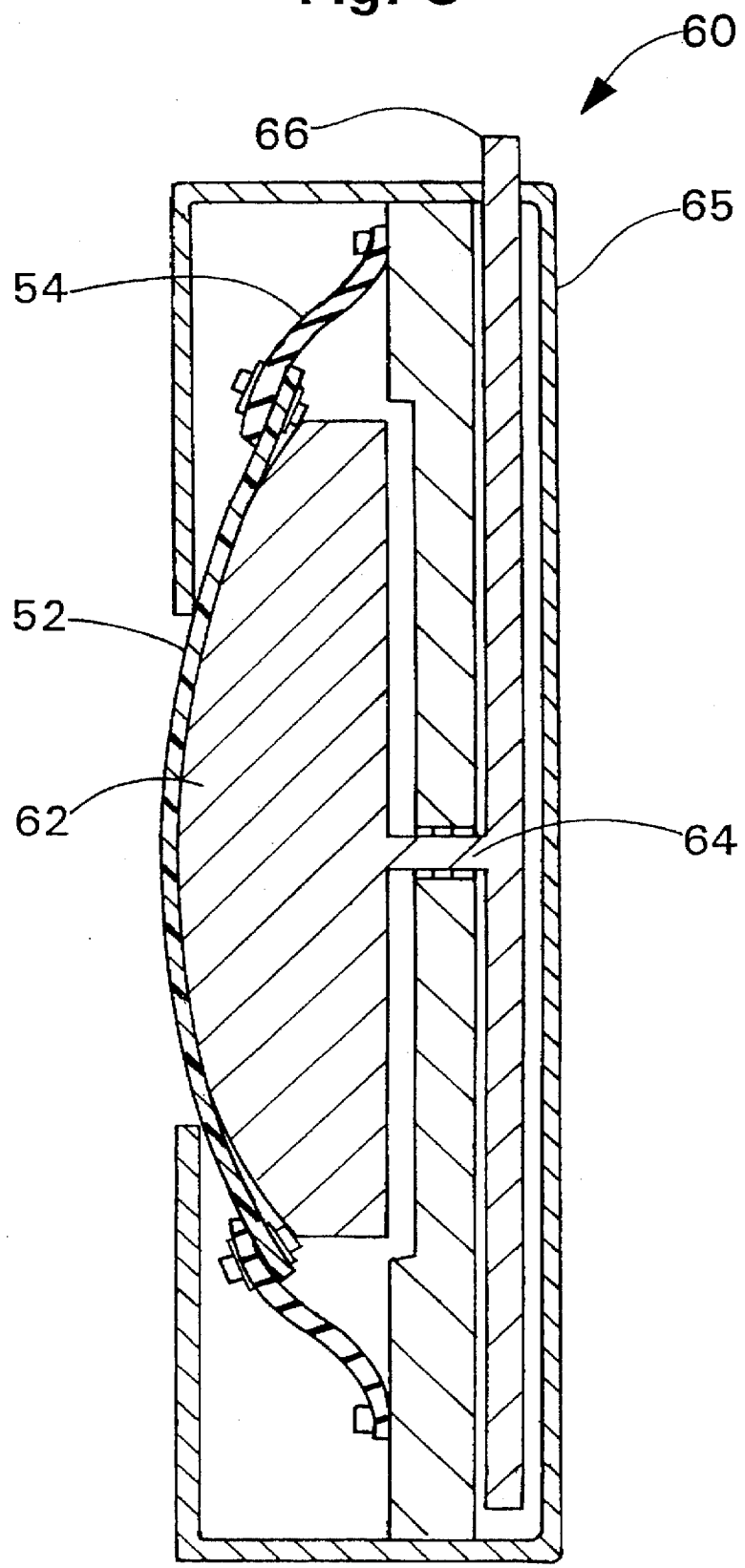
FIG. 8 is a cross-sectional view of a third embodiment of the present invention viewing assembly.

Referring to FIG. 8, there is shown a third embodiment of the present invention viewing assembly 60, wherein the adjustable flexible body 28 shown previously in the embodiment of FIG. 6 is replaced by a shaped static structure 62. In the shown embodiment, the reflective surface 52 is pulled taut over the static structure 62 by the elastic ring 54, whereby the reflective surface 52 conforms to the shape of the static structure 62. The static structure 62 can be made into any desired shape. As a result, the static structure 62 can be custom made to correct the vision deficiencies of a specific person. For example, if a person has a specific eyeglass prescription, a static structure 62 can be fabricated to match that prescription. The static structure 62 would thereby create a specific curvature in the reflective surface 52 that would optically correct a reflected image as needed. However, creating a static structure 62 for a specific person's optical requirements does not lend itself to mass production. As such, in a preferred embodiment, the static structure 62 is manufactured with a common toric curvature. Consequently, the reflective surface 52 is deformed to the toric curvature of the static structure 62, creating a corresponding corrected reflected image.

It will be understood that a toric surface has a different radius of curvature along each meridian on the surface. As such, when a toric curvature is applied to a mirror, the reflected image changes if the mirror is rotated about its center. In the shown embodiment, the static structure 62 is attached to a shaft 64. The shaft 64 is connected to an adjustment wheel 66 that extends beyond the housing 65 of the viewing assembly 60. As such, by manually rotating the adjustment wheel 66, the static structure 62 is rotated about its midaxis, via the shaft 64. As the static structure 62 is rotated, changes in the orientation of the static structure 62 are transferred to the reflective surface 52. The image reflected by the reflective surface 52 therefore changes as the static structure 62 moves below the reflective surface 52 and the curvature of the reflective surface 52 changes. By creating a toric curvature on the static structure 62, and providing a means to rotate the static structure 62 about its midaxis, the reflective toric surface 52 can be selectively adjusted to correct a large range of common optical deficiencies.

Figure 9:
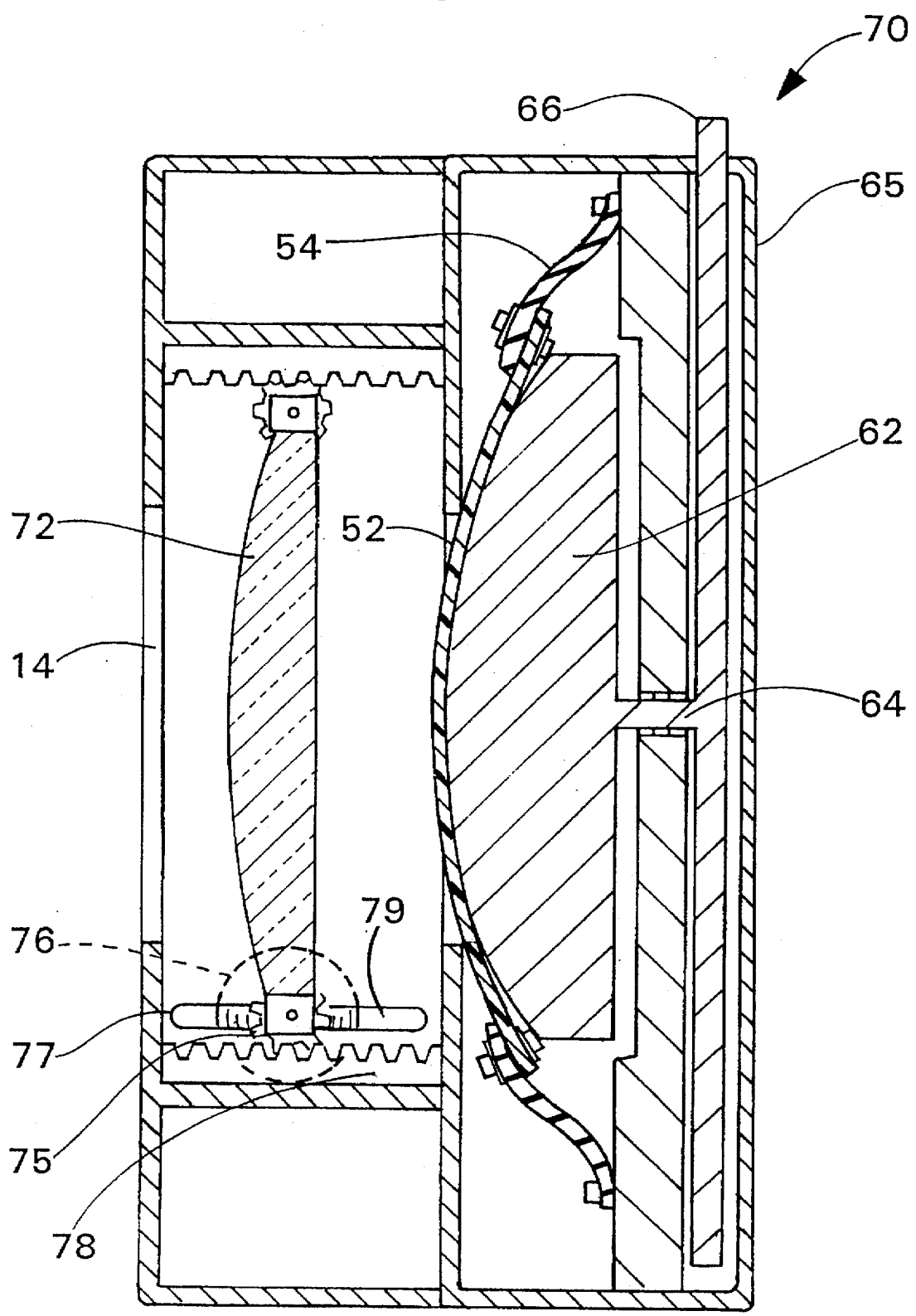
FIG. 9 is a cross-sectional view of a fourth embodiment of the present invention viewing assembly.

Referring to FIG. 9, there is shown a fourth embodiment of the present invention 70 wherein a corrective lens 72 is disposed in front of the reflective surface 52. The reflective surface 52 is held taut over a shaped static structure 62 by an elastic ring 54. As has been explained with previous embodiments, the reflective surface 52 therefore conforms to the shape of the static structure 62. In the shown embodiment, the static structure 62 is shaped to have a cylindrical curvature. As a result, the reflective surface 52 is also shaped to have a corresponding cylindrical curvature. The static structure 62 is coupled to be an adjustment wheel 66, via shaft 64. Consequently, as the adjustment wheel 66 is rotated, the static structure 62 rotates about its midaxis and curvature of the reflective surface 52 changes.

The corrective lens or optic element 72 is adjustably positioned in front of the reflective surface 52. The corrective lens 72 can be either convex or concave to produce spherical corrections in an image reflecting off the reflective surface 62 and passing through the corrective lens 72. The corrective lens 72 may also be of the fresnel type without departing from the spirit and scope of the invention. In the shown embodiment, a pinion gear 75 is rotatably attached to the corrective lens 72. A shaft 77 passes through the center of the pinion gear 75 and joins the pinion gear 75 to an adjustment knob 76 on the exterior of the viewing assembly 70. The shaft 77, connecting the adjustment knob 76 to the pinion gear 75, passes through a slotted opening 79 in the housing 65. The pinion gear 75 rides along rack 78 inside the mirror housing 65. As such, the position of the corrective lens 72 relative the reflective surface 52 can be selectively adjusted, within the mirror housing 65, by rotating the adjustment knob 76 and moving the corrective lens 72 back and forth across the gear rack 78. By moving the corrective lens 72 back and forth in front of the reflective surface 52, a large range of toric corrections can be produced in a reflected image.

In the shown embodiment, a person would view a reflected image by looking through the view window 14 in the mirror housing 65. By looking through the view window 14, a person is able to see the portion of the reflective surface 52 that is pulled taut over the shaped static structure 62. The shaped static structure 62 produces a cylindrical curvature in the reflective surface 52. Consequently, the reflected image viewed from the reflective surface 52 is optically corrected according to the cylindrical curvature reproduced in the reflective surface 52. The cylindrically corrected reflective surface 52 is viewed through the corrective lens 72. The corrective lens 72 produces spherical corrections in the image reflected from the reflective surface 52. As a result, the reflected image is corrected both spherically, by the corrective lens 72, and cylindrically by the shape of the reflective surface 52.

As has been previously described, the cylindrical curvature of the reflective surface 52 can be selectively changed by rotating the static structure 62 below the reflective surface 52. Furthermore, the spherical corrections produced by the corrective lens 72 can be selectively altered by varying the position of the corrective lens 72 relative the reflective surface 52. The compound optical corrections that can be produced in the reflective toric image allow the viewing assembly 70 to be individually adjusted by the viewer to correct the reflected image as needed. In the shown embodiment, the corrective lens 72 creates spherical corrections in the viewed reflected image, while the static structure 62 creates cylindrical corrections in the reflective surface 52. However, it should be understood that the static structure 62 can be used to produce any desired corrections in the reflective surface 52. Similarly, the corrective lens 72 can be used to produce any desired secondary corrections in the reflected image. Consequently, any combination of optical corrections can be produced.

Referring to FIGS. 10–17, there is shown a fifth embodiment of the present invention viewing assembly, generally designated 100, for providing cylindrical, spherical and toric mirrored surfaces. The fifth embodiment is similar in principle to the first three embodiments in that a sheet of reflective material, such as MYLAR®, is disposed upon a flexible body preferably formed of an elastomeric material, such as silicone. The contour of the reflective surface/flexible body subassembly (hereafter, "the reflective body 102") is altered to change the shape of the reflective surface, thereby causing the desired optical effect on the front of the reflective surface. However, the structure for altering the contour of the reflective body 102 is different than the embodiments described above. To best illustrate the fifth embodiment, it is shown in FIGS. 10–17 without a face surface or housing and with a generally round or circular reflective body 102.

Figure 10:
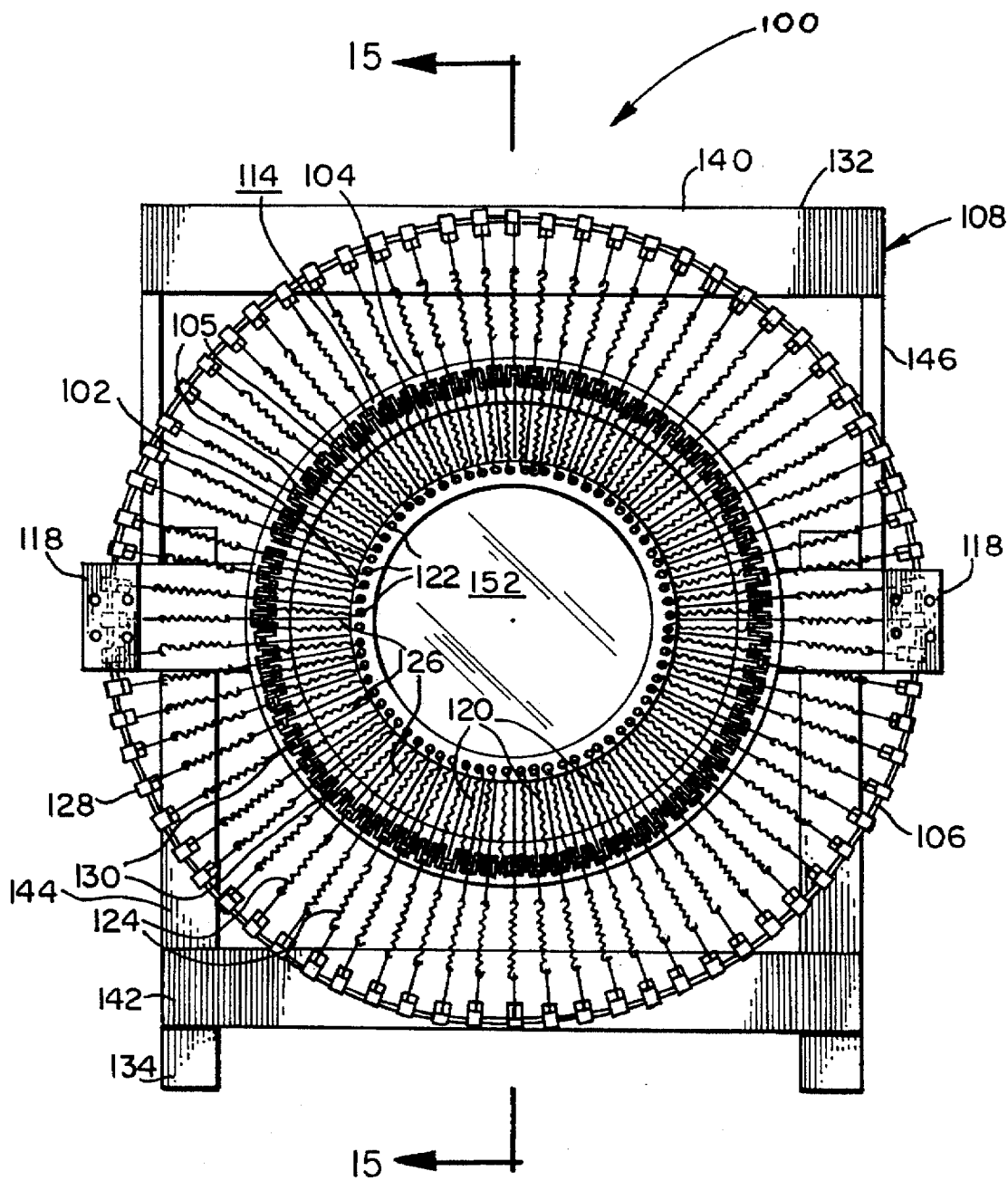
FIG. 10 is a front elevational view of a fifth embodiment of the present invention viewing assembly.
Figure 12:
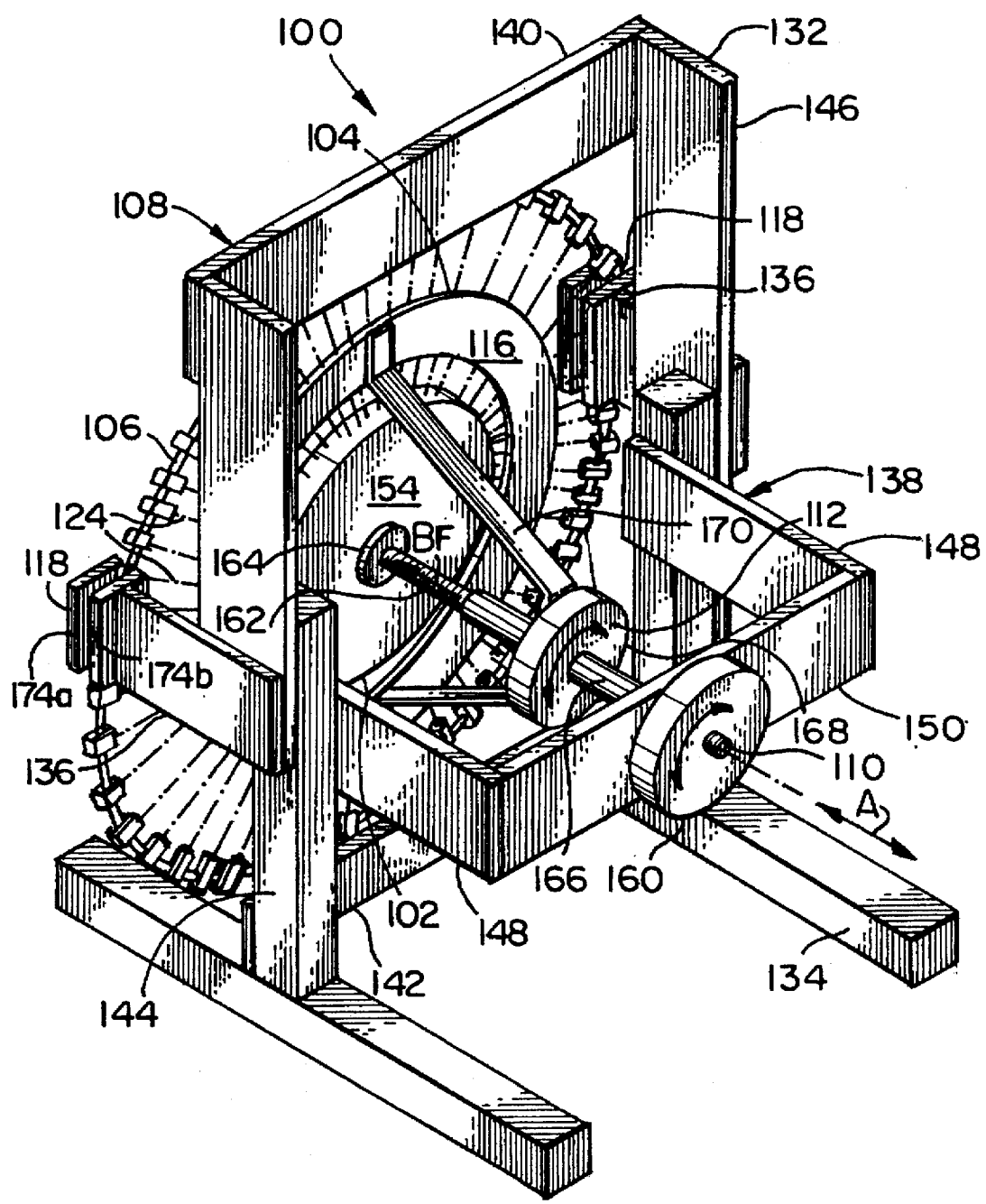
FIG. 12 is a rear perspective view of the fifth embodiment of the present invention viewing assembly.

Referring now to FIGS. 10 and 12, the viewing assembly 100 includes the generally circular reflective body 102, a flexible plate ring 104, a series of holders 105, a support ring 106, a frame 108, a spherical adjuster 110 and a cylindrical adjuster 112. The diameter of the flexible plate ring 104 is greater than the diameter of the reflective body 102, and the diameter of the support ring 106 is greater than the diameter of the flexible plate ring 104. The reflective body 102 has a front reflecting surface 152 and a rear surface 154. The flexible plate ring 104 has a front surface 114 and rear surface 116. The series of holders 105 are spaced along, and fastened to, the front surface 114 at even intervals. The series of holders 105 and the front surface 114 of the flexible plate ring 104 are visible in FIG. 10, whereas the adjusters 110 and 112 and the rear surface 116 of the flexible plate ring 104 are visible in FIG. 12. The support ring 106 is connected to the frame 108 by two mounting plate and bracket assemblies 118 on opposing sides of the support ring 106.

Referring now to FIGS. 10 and 11, there is shown the manner in which the reflective body 102 is attached to the remaining parts of the viewing assembly 100. The reflective body 102 is attached to the flexible plate ring 104 and the support ring 106 through a series of radially extending biasing members and wires, best illustrated in FIG. 11 and described in more detail below. The reflective body 102 is attached to the flexible plate ring 104 by a set of radially extending first biasing members 120. A series of mechanical fasteners, such as metal grommets 122, extend around the periphery of the reflective body 102. That is, the grommets 122 are secured to the sheet of reflective material 186 at a position radially outward of the main body of the reflection body 102. The set of first biasing members 120 connect at a first end to the grommets 122 with a simple hook connection, extend radially outward from the periphery of the reflective body 102 and connect at a second end to the holders 105 with a simple hook connection. In this manner, the reflective surface 152 iof the reflective body 102 is kept in constant and even radial tension by the set of first biasing members 120.

Figure 14:
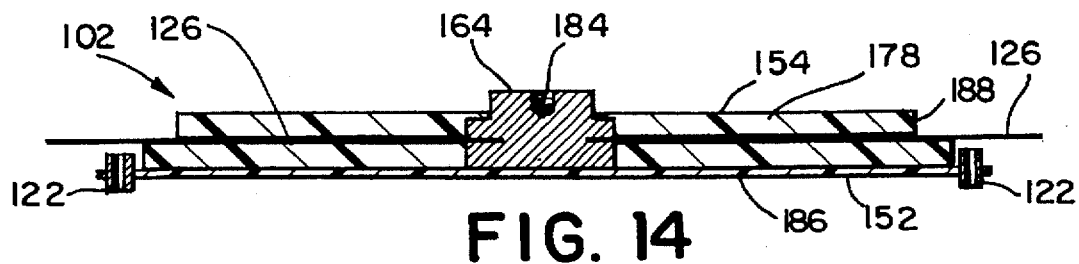
FIG. 14 is a cross-sectional view of FIG. 13, taken along line 14—14 of FIG. 13.

The reflective body 102 is also attached to the support ring 106 by a combination of a set of radially extending second biasing members 124 and a set of radially extending wires 126. A first end of each wire 126 is embedded within the flexible body portion of the reflective body 102, as best illustrated in FIG. 14, described below. Each second biasing member 124 is connected at a first end by a hook connection to a second end of a wire 126 to form a single radially extending piece. A second end of each second biasing member 124 is attached by a clip 128 to the support ring 106, as described in more detail below. The lengths of the wires 126 and second biasing members 124 are selected so that the wires 126 extend through and slightly past the flexible plate ring 104 before they connect to the respective biasing members 124. The wires 126 pass through guide holes 130 in the holders 105 such that the flexible plate ring 104, support ring 106 and the reflective body 102 flex like a single body, as described in more detail hereinafter.

In the fifth embodiment of the invention, it is preferred that the set of first and second biasing members 120 and 124 be coil springs. However, the biasing members 120 and 124 may be constructed of any suitable material which flexes in a reciprocal manner, such as strips of elastomeric material.

In the fifth embodiment of the invention, the wires 126 are generally flat, such that the wires 126 are generally rectangular in cross section and are preferably constructed of a high strength flexible material, such as spring steel. Although other materials and shapes could be used, such as generally circular in cross-section music wire. However, flat wires provide a better contour adjustment to the reflective body 102 than round wire rods because flat wires contact a larger surface area of the flexible body portion of the reflective body 102 than round wire.

In the fifth preferred embodiment, there are seventy-two wires 126 and seventy-two first and second biasing members 120 and 124 spaced at approximately five degree intervals around the outer periphery of the reflective body 102. The large number of wires and biasing members allows for precise changes to be made to the shape of the front reflecting surface 152 to maintain high optical quality. However, it is within the scope of the invention to simplify the tensioning scheme by either providing a smaller number of wires and biasing members, or by providing alternative methods of tensioning with a simpler construction and/or less parts.

Referring now to FIGS. 10 and 12, the viewing assembly frame 108 includes a generally rectangular framing portion 132, a base 134, two forwardly extending beams 136 and a rearwardly extending portion 138. The rectangular framing portion 132 has an upper beam 140, a lower beam 142 and opposite side beams 144 and 146. The rectangular framing portion 132 is secured to the base 134. The forwardly extending beams 136 extend from a mid-region of respective side beams 144 and 146 to the support ring 106 and at their distal ends are connected to the support ring 106 by the mounting plate and bracket assemblies 118, as described in more detail below. The rearwardly extending portion 138 of the frame 108 has rearwardly extending beams 148 which extend backwards from a mid-region of the respective side beams 144 and 146, and a bracket 150 connecting the rearward ends of the two side beams 144 and 146.

The various elements of the viewing assembly frame 108 are secured together using standard fasteners, such as nuts and bolts (not shown) in a manner not pertinent to the present invention and well understood by those of ordinary skill in the art. It is also understood by those of ordinary skill in the art from this disclosure that the various elements of the viewing assembly frame 108 could be interconnected in other manners, such as with welding or adhesives, and the viewing assembly frame 108 could be of single-piece construction. Similarly, the various elements of the viewing assembly 108 are preferably constructed of a high-strength lightweight material, such as aluminum. However, other materials, such as a polymeric material, could be used without departing from the spirit and scope of the invention.

The viewing assembly frame 108 depicted in FIGS. 10 and 12 allows the viewing assembly 100 to stand stably on a surface. However, the viewing assembly 100 may be mounted to a wall or suspended in some other manner to a frame. Accordingly, certain portions of the frame 108, including the base 134 and portions of the rectangular framing portion 132 (the upper beam 140, lower beam 142 and upper and lower portions of the side beams 144 and 146), are not necessarily required to allow the viewing assembly 100 to perform its functions.

Referring now to FIG. 11, as mentioned above, the outer periphery of the reflective surface 152 is ringed with grommets 122. The set of first biasing members 120 extend between the grommets 122 and the holders 105 attached to the flexible plate ring 104. The holders 105 include a base 105a which is in facing engagement with the front surface 114 of flexible plate ring 104. A pair of spaced-apart side walls 105b extend away from the base 105a in a forward direction. A rod 105c extends between the side walls 105b and is spaced from the base 105a to form the guide hole 130. That is, the guide holes 130 are formed between the base 105a, side walls 105b and rod 105c. Each holder 105 is secured to the flexible plate ring 104 by a standard fastener (not shown), such as a screw extending through the back surface of the flexible plate ring 104 to the base 105a of the holder 105, although the holders 105 could be secured to the flexible plate ring 104 in other manners, such as with rivets, an adhesive or through welding.

The flexible plate ring 104 is preferably constructed of a flexible high-strength material, such as carbon-fiber or fiberglass. The holders 105 are preferably constructed of a high-strength material, such as aluminum, although other materials could be used to construct the flexible plate ring 104 and holders 105, without departing from the spirit and scope of the invention.

For convenience of assembly, one pair of adjacent first biasing members 120 are fastened to alternating holders 105. This is, a U-shaped connector 147 extends around the side walls 105b and the radially outwardmost portion of the base 105a. One pair of adjacent first biasing members 120 are connected to the terminal portion of each U-shaped connector 147 with a simple hook connection. Thus, no first biasing members 120 are fastened to the remaining alternating holders 105. Obviously, the fastening arrangement may be modified so that one biasing member 120 is associated with each holder 105.

Figure 13:
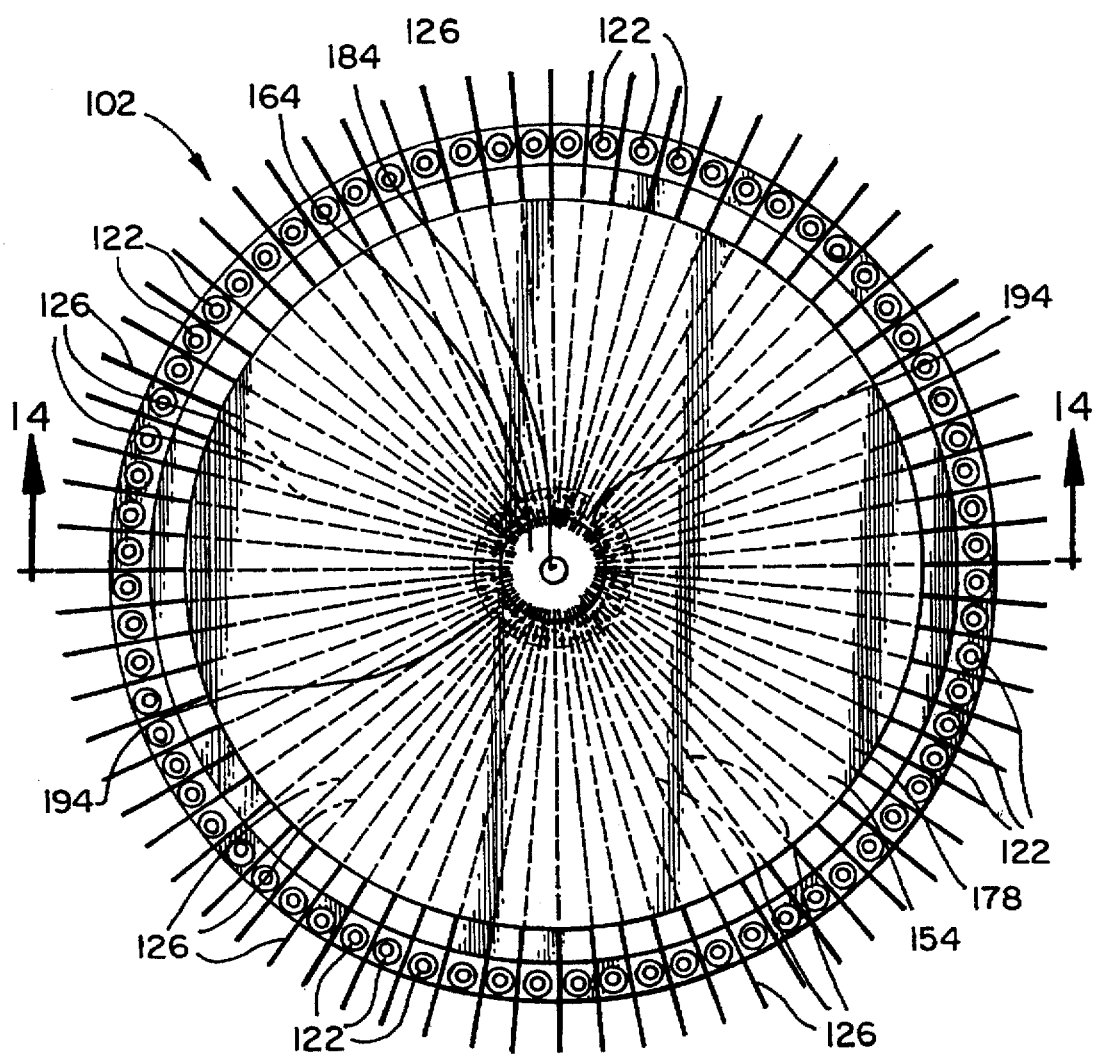
FIG. 13 is a rear elevational view of a reflective body associated with the fifth embodiment of the present invention viewing assembly.

The set of wires 126 extend from a center region of the back side of the reflective body 102 (as shown in FIG. 13), through the guide holes 130 in the holders 105, to the first ends of the set of second biasing members 124 with a simple hook connection. The second ends of the set of second biasing members 124 attach to the clips 128 spaced along the support ring 106. The clips 128 are generally trapezoidal-shaped in elevational view and include a slot 128a in the radially-outermost surface for receiving the supporting ring 106 in a complementary manner. A standard fastener, such as a pin 128b extends through the support ring 106 and each clip 128 to secure each clip 128 to the support ring 106. A pivoting linkage 128c extends radially inwardly from each clip 128 and is secured to the second end of the second biasing member 124 with a simple hook connection. The support ring 106 and clips 128 are preferably made of the same materials as the flexible plate ring 104 and holders 105, respectively.

It is understood by those of ordinary skill in the art from this disclosure that the present invention is not limited to any particular arrangement of maintaining the reflective body 102 taught. That is, other less complicated or more sophisticated arrangements could be used without departing from the spirit and scope of the invention.

Referring now to FIGS. 11, 12 and 16, the support ring 106 is secured to the frame 108 by the mounting plate and bracket assemblies 118. Each mounting plate and bracket assembly 118 includes a front plate 174a and back plate 174b and four fastening bolts 178 extending therebetween. The back plate 174b is secured to the forwardly extending beam 136 and the support ring 106 and clips 128 are sandwiched between the front and back plates 174a, 174b, as best shown in FIG. 16. However, it is understood by those of ordinary skill in the art from this disclosure that the support ring 106 can be secured to the frame 108 in other manners. For instance, the support ring 106 could be welded to the frame 108 or secured to the back plate 174b with U-shaped bolts (not shown).

Referring now to FIGS. 13 and 14, there is shown the construction of the reflective body 102, separate from the remaining parts of the viewing assembly 100. The reflective body 102 includes a sheet of reflective material 186, a flexible body portion 178, wires 126 and a hub 164. The rear of the flexible body portion 178 defines the previously identified rear surface 154 of the reflective body 102, whereas the front of the sheet of reflective material 186 defines the previously identified front reflecting surface 152 of the reflective body 102. A portion of the wires 126 and most of the hub 164 are embedded in the flexible body portion 178. In FIG. 13, the embedded portion of the wires 126 and hub 164 are shown with dashed lines because they are not visible in a rear view. The wires 126 extend into complementarily sized radially extending bores spaced around the periphery of the hub 164, like spokes on a wheel. Transversely extending set screws 194 are used to secure each wire 26 within its corresponding bore. A rear portion of the hub 164 extends beyond the rear surface 154 of the reflective body 102. The rear center of the hub 164 includes a threaded hole 184 for receiving the threaded shaft 162 (not shown in FIG. 13) associated with the spherical adjuster 110, described in more detail hereinafter.

As noted above, one material suitable for use as the sheet of reflective material 186 is a thin metal coated polymer, such as aluminized polyesters or MYLAR®. A preferred material for the flexible body portion 178 is an elastomeric material, such as silicone or GERTV. However, it is understood by those skilled in the art that the flexible body portion 178 could be constructed of other flexible or formable materials, such as isoprene rubbers, natural rubbers, CIS polyisoprene rubbers, neoprene rubbers, butyl rubbers, nitrile copolymers, hypalon, acrylic, thiokol or polyurethane.

One method for constructing a reflective body 102 is as follows:

1. A sheet of reflective material 186 is laid flat.
2. A flexible plate ring 104/holder 105 subassembly is placed around the sheet of reflective material 186.
3. A set of first biasing members 120 are connected to the grommets 122 and holders 105 to tension the sheet of reflective material 186. That is, the first set of biasing members 120 pull the sheet of reflective material 186 taut around its periphery.
4. A circular mold in the form of a plastic dam (not shown) is placed on top of the sheet of reflective material 186. The side edges of the mold include holes for the set of wires 126 to pass therethrough. The mold is shaped to form a shoulder 188 in the flexible body 178.
5. A set of wires 126 are passed through the holes in the dam and attached to a hub 164.
6. A sufficient quantity of silicon is poured into the mold to completely cover the set of wires 126 and most of the hub 164. The silicon self-adheres to the sheet of reflective material 186. One suitable type of moldable silicon is HS IV RTV High Strength Moldmaking Silicone Rubber and Thixo Additive manufactured by Dow Corning Corporation, although other flexible materials could be used without departing from the spirit and scope of the invention.
7. After the silicon sets, the reflective body 102 can be installed in the viewing assembly 100.

To achieve the most accurate contouring of the reflective body 102, the set of wires 126 should ideally meet in the center of the flexible body 178. To accomplish this, instead of using the hub 164, the wires 126 connect to each other at the center of the flexible body 178 through another method, such as welding, and the shaft 162 (not shown) associated with the spherical adjuster 110 is fixed to the center of the reflective body 102 by another method, such as welding to the wires 126.

Referring now to FIGS. 12 and 15, the flexible plate ring 104 generally lies in the same plane as the periphery of the reflective body 102 before any cylindrical or spherical adjustments are made to the reflective body 102, whereas the support ring 106 generally lies in a plane forward to the plane of the reflective body 102 before any cylindrical or spherical adjustments are made to the reflective body 102.

The spherical adjuster 110 includes a first nut 160 and a threaded inner shaft 162. The forward end of the inner shaft 162 is screwed into a hub 164 embedded in, and partially extending from, the center of the rear surface 154 of the reflective body 102. The inner shaft 162 extends through an opening in the bracket 150 without being threadably connected to the bracket 150. The first nut 160 screws onto the rearward end of the shaft 162. The support ring 106, flexible plate ring 104, first and second biasing members 120 and 124, frame 108 and first nut 160 are positioned so that there is a biasing force $B_F$ pulling the inner shaft 162 towards the front of the viewing assembly 100. Since the diameter of the first nut 160 is selected to be greater than the diameter of the opening in the bracket 150, the biasing force $B_F$ causes the first nut 160 to push against the bracket 150. The shaft/nut arrangement allows the inner shaft 162 to reciprocate or translate with respect to the first nut 160 along the mid-axis A, as the first nut 160 is turned. The inner shaft 162 does not rotate as the first nut 160 is turned because it is fixed to the hub 164. In particular, as the first nut 160 is turned in the clockwise direction as viewed from the rear of the viewing assembly 100, the inner shaft 162 moves rearward (or to the right in FIG. 15). As the first nut 160 is turned counterclockwise, the inner shaft 162 moves forward.

Since the inner shaft 162 is screwed into the hub 164, and since the periphery of the reflective body 102 is connected as described above to the fixed frame 108, a rearward movement of the inner shaft 162 (caused by turning the first nut 160 clockwise) causes a rearward movement of the hub 164 with respect to the periphery of the reflective body 102, and thus alters the contour of the reflective body 102 to be spherically concave. Accordingly, if the reflective body 102 is initially in a neutral position (i.e., no spherical correction), as shown in FIG. 15, the shape of the front reflecting surface 152 goes from having no spherical contour to being relatively spherically concave (i.e., having a radius of curvature). Additional clockwise movements of the first nut 160 decreases the diameter of the sphere.

Likewise, a forward movement of the inner shaft 162 (caused by turning the first nut 160 counterclockwise) causes a forward movement of the hub 164 with respect to the periphery of the reflective body 102, thereby altering the contour of the reflective body 102 in the opposite direction to increase the diameter of the sphere. The biasing force $B_F$ and the size and placement of the spherical adjuster 110 are selected so that the shaft 162 can translate forward and backward by a sufficient distance to create spherical adjustments within the range necessary to correct the vision of most people. The support ring 106, frame 108 and spherical adjuster 110 are arranged so that there is always a biasing force $B_F$ pulling the shaft 162 towards the front of the viewing assembly 100, even when the front reflecting surface 152 is planar or very concave to provide a very large spherical correction.

The cylindrical adjuster 112 includes a threaded outer shaft 166, a second nut 168 and opposite ears 170. The rearward end of the outer shaft 166 is rotatably fixed to the bracket 150. The outer shaft 166 surrounds the inner shaft 162 so that the inner shaft 162 telescopes within the outer shaft 166 but is not threadably connected to the outer shaft 166. The second nut 168 is threadably connected to the outer shaft 166. The opposite ears 170 join together at one end 170a which includes an aperture 170b which slidably receives the outer shaft 166. The one end 170a of the ears 170 abuts the second nut 168 but is not fixed to the second nut 168 such that the one end 170a is in sliding frictional engagement with the second nut 168. The radially outward ends of the ears 170 are attached to the rear surface 116 of the flexible plate ring 104 by a screw, clamp, fastener or the like (not shown).

In operation, turning the second nut 168 clockwise pushes the ears 170 forward (away from the bracket 150), which, in turn, pushes the upper and lower peripheral regions of the flexible plate ring 104 forward with respect to the hub 164 of the reflective body 102, thereby altering the contour of the reflective body 102. Since the ears 170 push against opposite peripheral regions of the reflective body 102, the contour of the reflecting body 102 is altered to change the shape of the front reflecting surface 152 in a concave, cylindrical manner. Thus, if the reflective body 102 is initially in a neutral position (i.e., the flexible plate ring 104 is located in a single plane to yield no cylindrical correction), and the second nut 168 is rotated clockwise, the shape of the front reflecting surface 152 goes from having no cylindrical contour to being relatively concave and cylindrical (i.e., having a cylindrical curvature).

Likewise, turning the second nut 168 counterclockwise causes the ears 170 to move backwards (towards the bracket 150) which, in turn, causes the upper and lower peripheral regions of the flexible plate ring 104 to move rearward with respect to the hub 164 of the reflective body 102, thereby altering the contour of the reflective body 102 in the opposite direction to increase the diameter of the cylinder.

The placement of the cylindrical adjuster 112 and related adjusting parts are selected so that when the ears 170 are in their maximum rearward or forward position, the biasing force on the reflective body 102 yields a cylindrical reflective surface necessary to correct the vision of most people who require a large optical correction.

From the description of FIGS. 10, 12 and 15 above, it should be clear that the contour of the reflective body 102 may be altered to create concave, spherical or cylindrical shape adjustments to the reflective surface 152, independent of each other. Concave toric curvatures may be created in the reflective surface 152 by combining spherical and cylindrical shape adjustments.

While the reflection surface 152 of the viewing assembly 100 of the fifth preferred embodiment can be adjusted to achieve concave, spherical and/or cylindrical shapes, it is understood by those skilled in the art that the reflection surface 152 can be adjusted to achieve convex, spherical and/or cylindrical shapes by axially securing the first knob 160 to the bracket 150 and the second knob 168 to the one end 170a of the ears 170, should such an optical correction be desired.

FIG. 17 shows diagrammatically how to adjust the axis of the viewing assembly 100. A rotation device 190 is connected by a shaft 192 to the viewing assembly 100. The rotation device 100 rotates the entire viewing assembly 100 about its midaxis to provide the desired axis correction indicated by a person's eyeglass prescription. The particular type of rotation device 190 is not pertinent to the present invention, as any suitable device, including both manual and power-type devices, could be used to rotate the viewing assembly 100.

While the foregoing description of the various embodiments of the viewing assembly discusses cylindrical, spherical and toric surfaces, it is understood by those skilled in the art that the present invention is not limited to configuring the reflective surface to have any particular shape. For instance, the reflective surface could be configured to have an aspherical or parabolic surface. Similarly, the reflective surface could be configured to reflect a magnified image as well as a corrected image. Alternatively, a magnifying lens could be placed in front of the reflective surface to magnify the reflected image.

In view of the multitude of differing embodiments described above, it should appear obvious that a person skilled in the art could combine elements for each embodiment and produce a viewing assembly not specifically described herein. It should therefore be understood that the embodiments described herein are merely exemplary and that a person skilled in the art may make such variations and modifications without departing from the spirit and scope of the invention. All possible combinations of the features of the disclosed embodiments and other obvious variations and modifications regarding differing physical geometric proportions, materials or functionally equivalent components are intended to be included within the scope of the invention as defined in the appended claims.

We claim:

1. A viewing apparatus comprising:
   (a) a flexible body having a reflective front surface for reflecting an image;
   (b) a first adjustment mechanism operatively engaged with the flexible body, the first adjustment mechanism varying the radius of curvature of the front surface of the flexible body such that the front surface is in the form of a partial sphere, thereby providing a spherical correction in the image;
   (c) a second adjustment mechanism, different from the first adjustment mechanism, operatively engaged with said flexible body, the second adjustment mechanism varying the curvature of the front surface of the flexible body such that the front surface is in the form of a partial cylinder, thereby providing a cylindrical correction in the image; and
   (d) a third adjustment mechanism operatively engaged with the flexible body rotating the flexible body about an axis extending through the flexible body to provide an axis correction in the image,
   wherein selective adjustments of the first, second, and third adjustment mechanisms provide one of either a spherical, cylindrical or toric correction in the image.

2. The apparatus according to claim 1 wherein the flexible body has an outer periphery which generally lies in a single plane when said reflective front surface is generally planar, the outer periphery defining opposite peripheral regions, the second adjustment mechanism applying force to the opposite peripheral regions in a direction generally perpendicular to the single plane.

3. The apparatus according to claim 1 wherein the flexible body has a center region, the first adjustment mechanism applying force against the center region of the flexible body.

4. The apparatus according to claim 1 wherein the flexible body has a midaxis extending through a center region of the flexible body generally perpendicularly with respect to the front reflecting surface when the front reflecting surface is generally planar and the third adjustment mechanism rotates the flexible body about the midaxis to provide an axis adjustment in the image.

5. A viewing apparatus comprising:
   (a) a flexible body having a reflective front surface for reflecting an image;
   (b) a first adjustment mechanism operatively engaged with the flexible body, the first adjustment mechanism comprising a flexible ring spaced from the flexible body and linked to the flexible body such that flexure of the ring results in flexure of the flexible body, the first adjustment mechanism varying the radius of curvature of the front surface of the flexible body such that the front surface is in the form of a partial sphere, thereby providing a spherical correction in the image; and
   (c) a second adjustment mechanism, different from the first adjustment mechanism, operatively engaged with said flexible body, the second adjustment mechanism varying the curvature of the front surface of the flexible body such that the front surface is in the form of a partial cylinder, thereby providing a cylindrical correction in the image,
   wherein selective adjustments of the first and second adjustment mechanisms provide one of either a spherical, cylindrical or toric correction in the image.

6. A viewing apparatus comprising:
   (a) a reflective body having a periphery, the reflective body comprising:
      (i) a flexible body portion,
      (ii) a flexible reflective front surface coupled to the flexible body portion for reflecting an image, and
      (iii) a plurality of wires embedded in the flexible body portion, the wires extending radially from a center region of the flexible body portion past the periphery of the of the reflective body, the wires terminating in ends;
   (b) a flexible ring spaced from and positioned radially outward of the reflective body and linked to the reflective front surface by a plurality of first biasing members, the flexible ring including a plurality of guide holes spaced around the ring, the wires extending through the guide holes;
   (c) a plurality of second biasing members extending radially from the wire ends;
   (d) a support ring spaced from and positioned radially outward of the flexible ring, the plurality of second biasing members extending between the wire ends and the support ring;
   (e) a frame having the support ring mounted thereto;
   (f) a spherical adjuster operatively engaged with the reflective body and the frame, the spherical adjuster applying force to the center region to move the center region with respect to the periphery of the reflective body, thereby varying the radius of curvature of the front surface of the flexible body such that the front surface is in the form of a partial sphere; and
   (g) a cylindrical adjuster operatively engaged with the flexible ring and the frame, the cylindrical adjuster applying force to diametrically opposed regions of the flexible ring to move the flexible ring with respect to the center region of the reflective body to cause flexure of the reflective body such that the front surface is in the form of a partial cylinder, whereby selective adjustments of the spherical and cylindrical adjusters provide one of either a spherical, cylindrical or toric correction in the image.

* * * * *